US006475488B1

(12) United States Patent
Pasqualini et al.

(10) Patent No.: US 6,475,488 B1
(45) Date of Patent: Nov. 5, 2002

(54) METHODS OF INHIBITING ANGIOGENESIS AND AMELIORATING CANCER BY USING SUPERFIBRONECTIN

(75) Inventors: Renata Pasqualini, Solana Beach, CA (US); Erkki Ruoslahti, Rancho Santa Fe, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 09/228,901

(22) Filed: Jan. 11, 1999

Related U.S. Application Data

(63) Continuation of application No. 08/717,169, filed on Sep. 20, 1996, now Pat. No. 5,922,676.

(51) Int. Cl.[7] .................. A61K 39/00; A61K 39/38; A61K 38/00; G01N 33/48
(52) U.S. Cl. .................. 424/185.1; 424/184.1; 436/64; 514/12
(58) Field of Search .................. 435/7.1, 7.2, 7.23; 436/64; 530/387.7, 387.9; 424/184.1, 185.1; 514/12

(56) References Cited

U.S. PATENT DOCUMENTS

| 4,728,637 A | * | 3/1988 | Silverman et al. | |
| 5,354,269 A | | 10/1994 | Goodheart et al. | 604/49 |
| 5,366,958 A | | 11/1994 | Weiner et al. | 514/2 |
| 5,629,291 A | * | 5/1997 | Ruoslahti et al. | |
| 5,747,452 A | * | 5/1998 | Ruoslahti et al. | |
| 5,922,676 A | * | 7/1999 | Pasqualini et al. | |

FOREIGN PATENT DOCUMENTS

| EP | 0207751 A1 | * | 6/1986 |
| WO | WO 90/13306 | * | 4/1989 |
| WO | WO 93/15203 | | 5/1993 |
| WO | WO 96/04304 | | 2/1996 |

OTHER PUBLICATIONS

Burgess et al., J of Cell Bio. 111:2129–2138, 1990.*
Irani MH (Database–GENESEQ, Accession No. R60021, National Center for Biotechnology Information, National Library of Medicine, Bethesda, Maryland, publicly available Feb. 23, 1995).*
Baralle, FE (Database–GENESEQ, Accession No. P70373, National Center for Biotechnology Information, National Library of Medicine, Bethesda, Maryland, publicly available Mar. 11, 1991).*
Geisow, MJ (Database–GENESEQ, Accession No. R08039 and, National Center for Biotechnology Information, National Library of Medicine, Bethesda, Maryland, publicly available Feb. 24, 1991).*
Jain, Scientific American, Jul. 1994.*
Gura, Science, v278, 1997, pp. 1041–1042.*
Zeeter, Annu. Rev. Med., 1998, v49. pp. 407–424.*
Spitler Cancer Biotherapy, 1995, 10:1–3.*
Takara Shuzo KK (Database–GENESEQ, Accession No. R20497, National Center for Biotechnology Information, National Library of Medicine, Bethesda, Maryland, publicly available May 8, 1992).*
Chan et al., *Science*, 251:1600–1602 (1991).
Giancotti et al., *Cell*, 60:849–859 (1990).
Hocking et al., *J. of Cell Biol.*, 133:431–444 (1996).
Koivunen et al., *Biotechnology*, 13:265–270 (1995).
Koivunen et al., *Methods in Enzymology*, 245:346–369 (1994).
Koivunen et al., *J. of Biol. Chem.*, 268:20205–20210 (1993).
Kornblihtt et al., *EMBO J.*, 4:1755–1759 (1985).
Montesano et al., *Cell*, 62:435–445 (1990).
Morla et al., *J. Cell. Biol.*, 118:421 (1992).
Morla et al., *Nature*, 367:193–196 (1994).
Pardoll, *Ann. Rev. Immunol.*, 13:399–415 (1995).
Pasqualini et al., *J. Cell. Biol.*, 125:447–460 (1994).
Chemical Abstracts, vol. 125, No. 23, Dec. 2, 1996, Columbus, Ohio, US; abstract No. 292488, XP002051534.
Saba and Cho, "Alteration of Tumor Growth by a Purified Alpha–2–Glycoprotein", *J. Reticuloendothelial Society*, vol. 22, No. 6, pp. 583–596 (1977).

* cited by examiner

*Primary Examiner*—Anthony C. Caputa
*Assistant Examiner*—Gary B. Nickol
(74) *Attorney, Agent, or Firm*—Campbell & Flores LLP

(57) ABSTRACT

The invention provides a method of inhibiting angiogenesis and treating pathologies with angioproliferative components. The invention provides a method of ameliorating tumor growth and metastasis in a subject comprising administering a superfibronectin or a superfibronectin-generating compound to the subject. The invention also provides a method of inhibiting the migration and attachment of tumor cells.

12 Claims, 21 Drawing Sheets

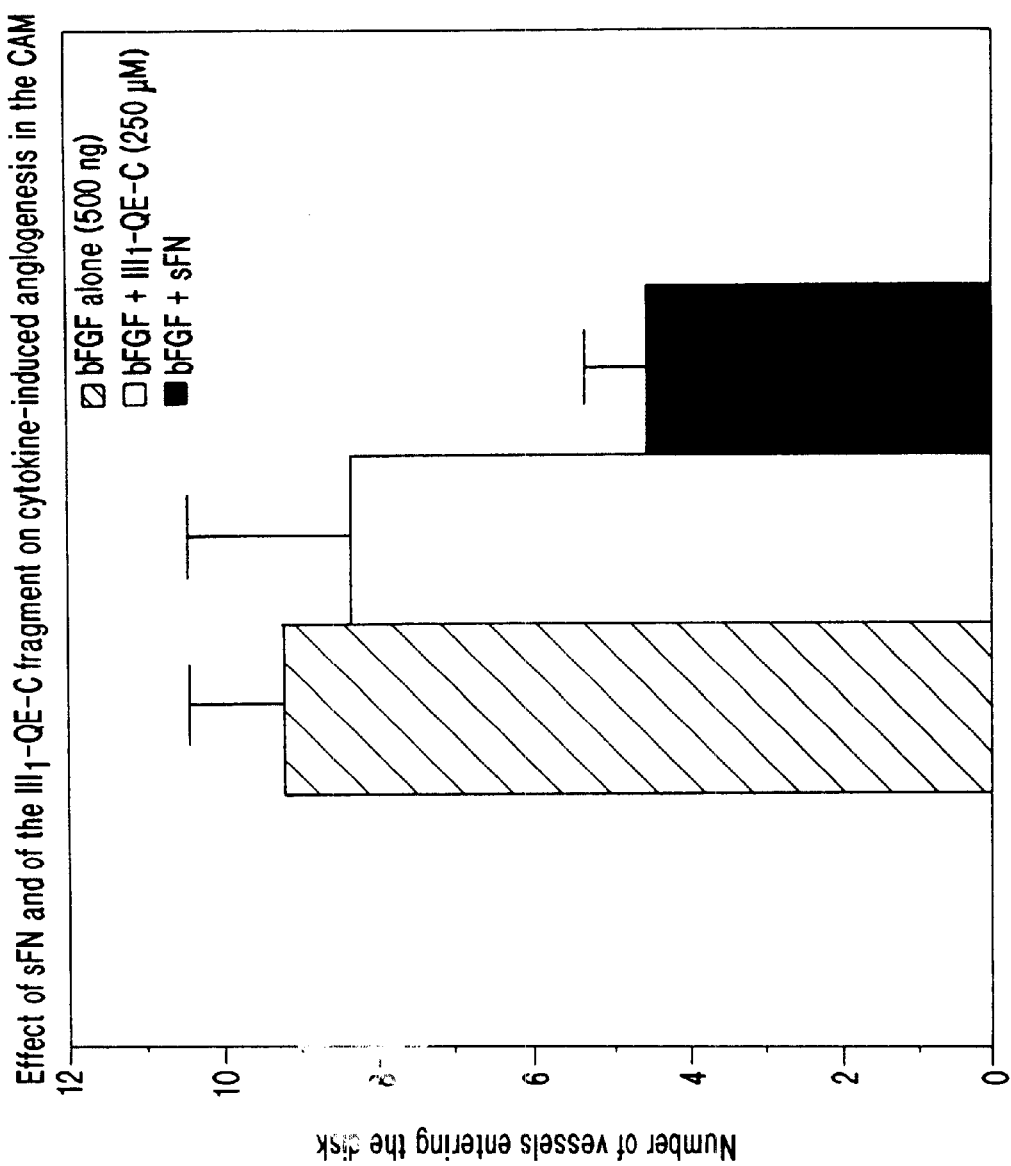

SEQUENCE LISTING

<160> NUMBER OF SEQ ID NOS: 21

<210> SEQ ID NO 1
<211> LENGTH: 109
<212> TYPE: PRT
<213> ORGANISM: Homo sapiens

<400> SEQUENCE: 1

Asn Ala Pro Gln Pro Ser His Ile Ser Lys Tyr Ile Leu Arg Trp Arg
1               5                   10                  15

Pro Lys Asn Ser Val Gly Arg Trp Lys Glu Ala Thr Ile Pro Gly His
            20                  25                  30

Leu Asn Ser Tyr Thr Ile Lys Gly Leu Lys Pro Gly Val Val Tyr Glu
        35                  40                  45

Gly Gln Leu Ile Ser Ile Gln Gln Tyr Gly His Gln Glu Val Thr Arg
    50                  55                  60

Phe Asp Phe Thr Thr Ser Thr Ser Thr Pro Val Thr Ser Asn Thr
65                  70                  75                  80

Val Thr Gly Glu Thr Thr Pro Phe Ser Pro Leu Val Ala Thr Ser Glu
                85                  90                  95

Ser Val Thr Glu Ile Thr Ala Ser Ser Phe Val Val Ser
                100                 105

<210> SEQ ID NO 2
<211> LENGTH: 96
<212> TYPE: PRT
<213> ORGANISM: Homo sapiens

<400> SEQUENCE: 2

Ser Gly Pro Val Glu Val Phe Ile Thr Glu Thr Pro Ser Gln Pro Asn
1               5                   10                  15

Ser His Pro Ile Gln Trp Asn Ala Pro Gln Pro Ser His Ile Ser Lys
                20                  25                  30

Tyr Ile Leu Arg Trp Arg Pro Lys Asn Ser Val Gly Arg Trp Lys Glu
            35                  40                  45

Ala Thr Ile Pro Gly His Leu Asn Ser Tyr Thr Ile Lys Gly Leu Lys
        50                  55                  60

Pro Gly Val Val Tyr Glu Gly Gln Leu Ile Ser Ile Gln Gln Tyr Gly
65                  70                  75                  80

His Gln Glu Val Thr Arg Phe Asp Phe Thr Thr Thr Ser Thr Ser Thr
                85                  90                  95

<210> SEQ ID NO 3
<211> LENGTH: 75
<212> TYPE: PRT
<213> ORGANISM: Homo sapiens

<400> SEQUENCE: 3

Asn Ala Pro Gln Pro Ser His Ile Ser Lys Tyr Ile Leu Arg Trp Arg
1               5                   10                  15

Pro Lys Asn Ser Val Gly Arg Trp Lys Glu Ala Thr Ile Pro Gly His
                20                  25                  30

Leu Asn Ser Tyr Thr Ile Lys Gly Leu Lys Pro Gly Val Val Tyr Glu
            35                  40                  45

Gly Gln Leu Ile Ser Ile Gln Gln Tyr Gly His Gln Glu Val Thr Arg
        50                  55                  60

Phe Asp Phe Thr Thr Thr Ser Thr Ser Thr Pro
65                  70                  75

<210> SEQ ID NO 4
<211> LENGTH: 31
<212> TYPE: PRT
<213> ORGANISM: Homo sapiens

<400> SEQUENCE: 4

Asn Ala Pro Gln Pro Ser His Ile Ser Lys Tyr Ile Leu Arg Trp Arg
1               5                   10                  15

Pro Lys Asn Ser Val Gly Arg Trp Lys Glu Ala Thr Ile Pro Gly
                20                  25                  30

<210> SEQ ID NO 5
<211> LENGTH: 34
<212> TYPE: PRT
<213> ORGANISM: Homo sapiens

<400> SEQUENCE: 5

Val Thr Ser Asn Thr Val Thr Gly Glu Thr Thr Pro Phe Ser Pro Leu
1               5                   10                  15

Val Ala Thr Ser Glu Ser Val Thr Glu Ile Thr Ala Ser Ser Phe Val
                20                  25                  30

Val Ser

<210> SEQ ID NO 6
<211> LENGTH: 56
<212> TYPE: PRT
<213> ORGANISM: Homo sapiens

<400> SEQUENCE: 6

-continued

Asn Ala Pro Gln Pro Ser His Ile Ser Lys Tyr Ile Leu Arg Trp Arg
1               5                   10                  15

Pro Lys Asn Ser Val Gly Arg Trp Lys Glu Ala Thr Ile Pro Gly His
            20                  25                  30

Leu Asn Ser Tyr Thr Ile Lys Gly Leu Lys Pro Gly Val Val Tyr Glu
        35                  40                  45

Gly Gln Leu Ile Ser Ile Gln Gln
    50                  55

<210> SEQ ID NO 7
<211> LENGTH: 89
<212> TYPE: PRT
<213> ORGANISM: Homo sapiens

<400> SEQUENCE: 7

Met Arg Gly Ser Asn Ala Pro Gln Pro Ser His Ile Ser Lys Tyr Ile
1               5                   10                  15

Leu Arg Trp Arg Pro Lys Asn Ser Val Gly Arg Trp Lys Glu Ala Thr
            20                  25                  30

Ile Pro Gly His Leu Asn Ser Tyr Thr Ile Lys Gly Leu Lys Pro Gly
        35                  40                  45

Val Val Tyr Glu Gly Gln Leu Ile Ser Ile Gln Gln Tyr Gly His Gln
    50                  55                  60

Glu Val Thr Arg Phe Asp Phe Thr Thr Thr Ser Thr Ser Thr Pro Gly
65                  70                  75                  80

Ser Arg Ser His His His His His
                85

<210> SEQ ID NO 8
<211> LENGTH: 94
<212> TYPE: PRT
<213> ORGANISM: Homo sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 9
<211> LENGTH: 27
<212> TYPE: DNA
<213> ORGANISM: Artificial Sequence
<220> FEATURE:
<223> OTHER INFORMATION: synthetic primer

<400> SEQUENCE: 9
ccggatccaa tgcaccacag ccatctc                                     27

<210> SEQ ID NO 10

```
<211> LENGTH: 27
<212> TYPE: DNA
<213> ORGANISM: Artificial Sequence
<220> FEATURE:
<223> OTHER INFORMATION: synthetic primer

<400> SEQUENCE: 10
ccggatccct gctggatgct gatgagc                                              27

<210> SEQ ID NO 11
<211> LENGTH: 28
<212> TYPE: DNA
<213> ORGANISM: Artificial Sequence
<220> FEATURE:
<223> OTHER INFORMATION: synthetic primer

<400> SEQUENCE: 11
ccggatccag gtgtgctggt gctggtgg                                             28

<210> SEQ ID NO 12
<211> LENGTH: 4
<212> TYPE: PRT
<213> ORGANISM: Homo sapiens

<400> SEQUENCE: 12

Met Arg Gly Ser
 1

<210> SEQ ID NO 13
<211> LENGTH: 10
<212> TYPE: PRT
<213> ORGANISM: Homo sapiens

<400> SEQUENCE: 13

Gly Ser Arg Ser His His His His His His
 1               5                   10

<210> SEQ ID NO 14
<211> LENGTH: 8
<212> TYPE: PRT
<213> ORGANISM: Homo sapiens

<400> SEQUENCE: 14

Gly Ser Pro Gly Ile His Arg Asp
 1               5

<210> SEQ ID NO 15
<211> LENGTH: 81
<212> TYPE: PRT
<213> ORGANISM: Homo sapiens
<220> FEATURE:
<221> NAME/KEY: VARIANT
<222> LOCATION: 5, 6, 7, 8, 9, 10, 11, 12, 13, 14, 15, 16, 17, 18, 19,
      20, 21, 22, 23, 24, 25, 26, 27, 28, 29, 30, 31, 32, 33, 34, 35,
      36, 37, 38, 39, 40, 41, 42, 43, 44, 45, 46, 47, 48, 49, 50, 51,
      52, 53, 54, 55, 56, 57, 58, 59, 60, 61, 62, 63
<223> OTHER INFORMATION: Xaa = Any Amino Acid
<220> FEATURE:
<221> NAME/KEY: VARIANT
<222> LOCATION: 64, 65, 66, 67, 68, 69, 70, 71
<223> OTHER INFORMATION: Xaa = Any Amino Acid

<400> SEQUENCE: 15

Met Arg Gly Ser Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa
             20                  25                  30
```

```
Xaa Xaa Xaa Xaa Xaa Xaa Xaa Xaa Xaa Xaa Xaa Xaa Xaa Xaa
        35                  40                  45
Xaa Xaa Xaa Xaa Xaa Xaa Xaa Xaa Xaa Xaa Xaa Xaa Xaa Xaa
        50                  55                  60
Xaa Xaa Xaa Xaa Xaa Xaa Xaa Gly Ser Arg Ser His His His His
        65                  70              75              80
His

<210> SEQ ID NO 16
<211> LENGTH: 6
<212> TYPE: PRT
<213> ORGANISM: Homo sapiens

<400> SEQUENCE: 16

Gly Arg Gly Asp Ser Pro
 1               5

<210> SEQ ID NO 17
<211> LENGTH: 11
<212> TYPE: PRT
<213> ORGANISM: Homo sapiens

<400> SEQUENCE: 17

Ala Cys Asp Cys Arg Gly Asp Cys Phe Cys Gly
 1               5                  10

<210> SEQ ID NO 18
<211> LENGTH: 9
<212> TYPE: PRT
<213> ORGANISM: Homo sapiens

<400> SEQUENCE: 18

Cys Arg Arg Glu Thr Ala Trp Ala Cys
 1               5

<210> SEQ ID NO 19
<211> LENGTH: 5
<212> TYPE: PRT
<213> ORGANISM: Homo sapiens

<400> SEQUENCE: 19

Ala Gln Asn Pro Ser
 1               5

<210> SEQ ID NO 20
<211> LENGTH: 5
<212> TYPE: PRT
<213> ORGANISM: Homo sapiens

<400> SEQUENCE: 20

Glu Glu His Gly Phe
 1               5

<210> SEQ ID NO 21
<211> LENGTH: 5
<212> TYPE: PRT
<213> ORGANISM: Homo sapiens

<400> SEQUENCE: 21

Ala Val Gly Asp Glu
 1               5
```

METHODS OF INHIBITING ANGIOGENESIS AND AMELIORATING CANCER BY USING SUPERFIBRONECTIN

This application is a continuation of application Ser. No. 08/717,169, filed Sep. 20, 1996, now U.S. Pat. No. 5,922,676, issued Jul. 13, 1999.

This invention was funded in part by NIH Grant Nos. CA62042 and CA30199. Accordingly, the United States government has certain rights in the invention.

BACKGROUND OF THE INVENTION

This invention relates generally to the field of angiogenesis and cancer therapy and more specifically to the use of superfibronectin and superfibronectin-generating compounds for the amelioration of pathologies with angioproliferative components, tumor cell growth and tumor metastasis.

Metastasis accounts for most deaths in cancer patients with solid tumors. The extent of tumor cell adhesion to the extracellular matrix and the stimulation of angiogenesis are critical steps in the metastatic process. Metastatic potential depends upon a complex series of events, including interactions of malignant tumor cells with extracellular matrix. Cellular adhesion to the extracellular matrix is primarily mediated by integrins, cell surface receptors which comprise an expanding family of transmembrane heterodimers of an $\alpha$ and a $\beta$ subunit. The identity of the subunits usually determines the receptor's functional specificity.

Several lines of evidence indicate that integrins play a key role in the malignant behavior of neoplastic cells. First, it has been demonstrated that integrin expression can change following viral or oncogenic transformation and that such alterations can affect the regulation of cellular protease cascades and tumor progression. Second, overexpression of $\alpha5\beta1$ in Chinese hamster ovary cells and of $\alpha2\beta1$ in human breast carcinoma cells has been shown to suppress tumorigenesis. Giancotti, F. G., et al., *Cell* 60:849–859 (1990). Third, inhibition of tumorigenicity and metastasis has been observed upon selective blocking of integrin function by RGD-containing peptides, which mimic integrin ligand binding sites. Inhibition of tumorigenicity and metastasis has been observed upon selective blocking of integrin function with function-blocking antibodies against individual $\alpha$ and $\beta$ subunits. Finally, the heterologous expression of the $\alpha2$ subunit in RD human rhabdomyosarcoma cells has been shown to profoundly alter their metastatic pattern, while the transfer of $\alpha4$ into murine B16 melanoma cells suppressed their ability to produce pulmonary metastasis. Chan, B. M. C., et al., *Science* 251:1600–1602 (1991).

The steps of the metastatic process in which integrins may play a role include detachment from the primary tumor and penetration of adjacent extracellular matrices and blood vessels; interaction with platelets and leukocytes in the circulation; and arrest and extravasation in the target organ. Giancotti, F. G., et al, *Biochem. Biophys. Acta* 1198:47–64 (1994).

One of the most important integrin ligands and a major component of extracellular matrix is fibronectin. Superfibronectin (sFN) is a polymeric fibrillar form of fibronectin which may be related to the natural matrix form of fibronectin. Compared to fibronectin, sFN has greatly enhanced cell adhesive properties. Whereas cells attach to fibronectin through integrins, cell attachment to sFN is mediated by both integrins and other distinct receptors. sFN can be produced in vitro by the incubation of fibronectin with fibronectin fragments. Morla, A., et al., *Nature* 367:193–196 (1994).

The growth of solid tumors and the metastatic process is dependent on vascularization of the tumor, a process called angiogenesis. Angiogenesis involves cytokine-mediated activation of blood vessel endothelial cells. Endothelial cells so activated are capable of forming entire capillary networks. In humans, a tumor which is not able to stimulate its own vascularization, i.e. is not angiogenic, may for years be restricted in growth to a few $mm^3$ and be limited to a million or less cells in size. Stimulation of blood vessel growth, i.e. the conversion of a tumor to an angiogenic phenotype, involves a change in the local balance of blood vessel growth inhibitors and growth stimulators. In addition to allowing a tumor to increase in size, this ingrowth of blood vessels also provides a means for tumor cell metastasis. Therefore, there is a need for factors which inhibit endothelial cell growth and angiogenesis, thereby having an antitumor effect by inhibiting tumor growth, causing tumor regression and inhibiting metastasis.

Factors which inhibit the growth and migration of endothelial cells can be used to treat diseases with angiogenic components, such as ocular neovascularization due to macular degeneration, diabetic retinopathy, rheumatoid arthritis, psoriasis, granulomas, granulation tissue and the like. Factors which inhibit the growth and migration of endothelial cells can also be used to inhibit or cause regression of the growth of tumors of the blood vessels, such as hemangiomas, sclerosing angiomas, Kaposi's sarcoma, lymphangioma, glomangioma, angiosarcoma, hemangioendotheliomas and the like.

There thus exists a need for agents for therapeutic intervention which can be used in the treatment and inhibition of angiogenesis, tumor growth and metastasis. This invention satisfies these needs and provides related advantages as well.

SUMMARY OF THE INVENTION

The present invention provides a method of ameliorating angiogenesis and treating pathologies with an angioproliferative component by administering superfibronectin (sFN) or a superfibronectin-generating compound to the subject. The pathologies can include, for example, cancer, and also ocular neovascularization, diabetic retinopathy, rheumatoid arthritis, psoriasis, granuloma and granulation tissue. It also provides a method of treating cancer by ameliorating tumor metastasis and tumor cell growth in a subject. In particular, the methods provide for inhibition of the metastasis of osteosarcoma, melanoma, and epithelial tumor cells such as colon, breast or ovarian carcinoma. In addition, the invention provides a method of inhibiting tumor cell attachment and migration.

BRIEF DESCRIPTION OF THE DRAWINGS

FIGS. 3A-1, 3A-2, 3B-1, 3B-2, 3C-1 and 3C-2 demonstrate that intravenously circulating tumor cells exposed to sFN are inhibited from metastasizing.

FIGS. 4A-1, 4A-2, 4B-1, 4B-2, 4C-1, 4C-2 and 4D demonstrate: that intraperitoneally injected sFN causes a specific and significant decrease in experimental metastasis, specifically, in the number of lung metastatic foci resulting from tumor cells injected intravenously; and, that intraperitoneally administered sFN inhibited spontaneous metastasis from pre-established tumors.

FIGS. 6A, 6B and 6C show that treatment with sFN and sFN-generating fragment $III_1$-QE-C (SEQ ID NO:7) can result in the regression of hemangioma, i.e. that sFN can suppress the growth of endothelially derived tumors. FIG. 6D demonstrates that a human breast carcinoma is sensitive to ex vivo treatment with $III_1$-QE-C (SEQ ID NO:7) and sFN. FIG. 6E demonstrates that an established subcutaneous tumor regresses as a result of local injections of sFN.

FIGS. 7A-1, 7A-2, 7B-1 and 7B-2 demonstrate that sFN suppresses both tumor cell spreading and tumor cell migration, specifically, after preincubation with sFN, tumor cells are unable to spread or migrate on any of the immobilized human extracellular matrix proteins fibronectin, laminin, collagen IV, and vitronectin or on BSA.

FIG. 9 demonstrates that sFN can inhibit the formation of new blood vessels, i.e. angiogenesis.

DETAILED DESCRIPTION OF THE INVENTION

Figure 1:
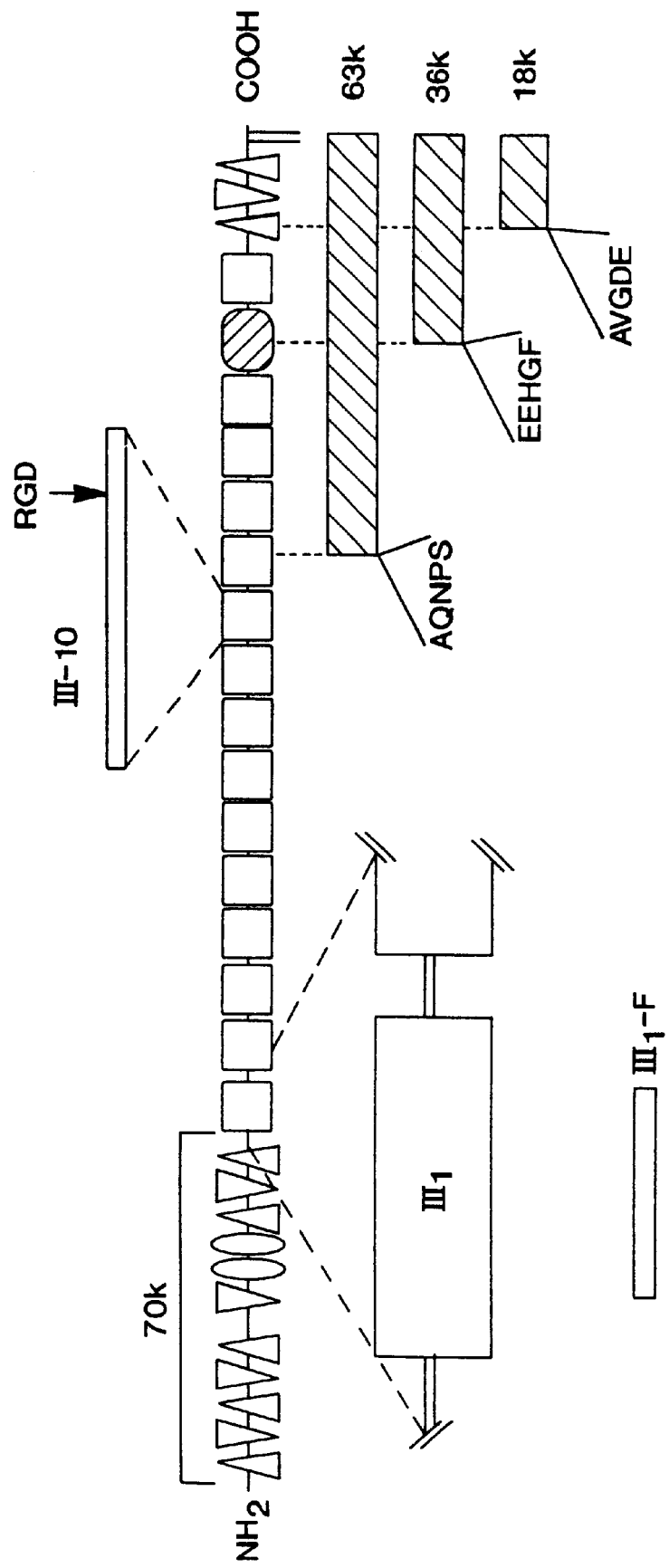
FIG. 1 demostrates the sections of the fibronectin molecule corresponding to symthetic and recombinant fragments, including III$_1$-derived symthetic and recombinant polypeptides containing the following amino-terminal sequences AQNPS (SEQ ID NO: 19), EEHGF (SEQ ID NO: 20) and AVGDE (SEQ ID NO: 21).

The invention provides a method of ameliorating angiogenesis and treating the angioproliferative component of a pathology by administering superfibronectin (sFN) or a superfibronectin-generating compound to a subject. The pathologies can include, for example, ocular neovascularization, diabetic retinopathy, rheumatoid arthritis, psoriasis, granuloma and granulation tissue.

The present invention provides a method of treating cancer by ameliorating tumor metastasis and tumor cell growth in a subject by administering superfibronectin (sFN) or a superfibronectin-generating compound to the subject. The method of the invention can inhibit or prevent the metastasis of circulating tumor cells or established solid tumors. The method is useful in treating, for example, osteosarcomas, melanomas, epithelial tumors such as colon, breast or ovarian carcinomas in a subject, and vascular cell tumors such as hemangiomas, Kaposi's sarcoma, lymphangioma, glomangioma, angiosarcoma and hemangioendotheliomas.

The invention further provides pharmaceutical compositions comprising sFN with a pharmaceutically acceptable carrier and a sFN-generating compound with a pharmaceutically acceptable carrier.

In addition, the invention provides a method of inhibiting integrin-mediated cell spreading and migration on various extracellular matrix substrates in vitro and in vivo. While sFN may ameliorate metastasis, tumor cell growth and angiogenesis by paralyzing adherence and/or migration mechanisms of cells, no method of the invention is limited by the different possible mechanisms of action.

In the following description, reference will be made to various methodologies known to those skilled in the art of molecular genetics, microbiology and general biology. Unless defined otherwise, all technical and scientific terms used herein have the same meaning as is commonly understood by one of skill in the art to which this invention belongs. In the description that follows, a number of terms used in biotechnology are extensively utilized. In order to provide a clear and consistent understanding of the specification and claims, including the scope to be given such terms, the following definitions are provided.

As used herein, the term "superfibronectin" or "sFN" refers to multimers of fibronectin of high relative molecular mass, polymeric fibrillar forms of fibronectin and high molecular weight aggregates of fibronectin, which may be related to the natural extracellular matrix form of fibronectin, as described in Morla, A., et al., *Nature* 367:193–196 (1994), which is incorporated herein by reference.

Functionally, compared to fibronectin, sFN has greatly enhanced cell adhesive properties. This increase in adhesion, which can be as great as ten-fold, can be measured and quantified, as described in Morla, A., et al., supra. Cell migration is also measurably reduced by sFN and can be quantitated using a "wound assay" as described in Morla, A., et al., supra.

sFN can be a product of the aggregation or cross-linking of fibronectin into high molecular weight forms. While the multimers can be formed by treating soluble fibronectin with fibronectin polypeptide fragments, as described for example by Morla, A., et al., supra, sFN also includes high molecular weight aggregates of fibronectin formed by any process or mechanism of aggregate formation. sFN aggregates can form with or without intermolecular covalent crosslinking, or any combination thereof. sFN or its components can be purified or synthesized from natural, synthetic, or recombinant sources or a combination thereof.

sFN includes modified forms of sFN or its constituent fibronectin fragments so long as they retain biological activity. Useful modifications can be identified using the adhesion assay and wound assay described in Morla, A., et al., supra, and the Examples described herein.

As used herein, the term "superfibronectin-generating compound" refers to any polypeptide having the property of enhancing the formation of sFN. A sFN-generating compound of the invention enhances the formation of multimers of fibronectin of high relative molecular mass; polymeric fibrillar forms of fibronectin; high molecular weight aggregates of fibronectin; fibronectin-fibronectin binding; or, fibronectin-fibronectin intermolecular associations. sFN generation can be enhanced in vitro and/or in vivo. The compound can be a recombinantly or synthetically derived polypeptide.

As used herein, the term "cancer" means any tumor, any benign or chronic neoplastic growth or any uncontrolled cell growth.

As used herein, the term "pathology with an angioproliferative component" means any pathological process involving endothelial cell or blood vessel growth, including benign or chronic diseases, such as cancer, diabetic retinopathy, hemangioma, rheumatoid arthritis, psoriasis, granuloma, granulation tissue and the like.

As used herein, the term "angiogenesis" means any growth of blood vessels or any neo- or re-vascularization of a tissue. The growth may or may not be stimulated by cytokines, such as cytokine-mediated activation of blood vessel endothelial cells.

As used herein, the terms "metastasis" and "metastases" refer to the movement of a tumor cell from its primary site by any means or by any route, including local invasion, lymphatic spread, vascular spread or transcoelomic spread.

As used herein, the terms "ameliorating" and "amelioration" mean any decrease in the growth rate or length of life of a cell, including any decrease in the rate of tumor cell growth or diminution in cell number. These terms include any lessening of the chance of occurrence or recurrence. These terms include inhibition and prevention of abnormal cell growth and metastasis. For example, sFN or a sFN-generating compound would be considered effective in its ability to ameliorate a tumor cell growth, a metastatic event or a pathology with an angiogenic component even if this ability was not totally effective. A sFN or a sFN-generating compound would be considered effective in its ability to slow cell growth even if the cell growth was not totally inhibited or the total effect did not cause a regression.

As used herein, the term "tumor cell migration" means any abnormal movement of a cell, including movement across other cells, extracellular matrices or through body fluids.

As used herein, the term "attachment" refers to means by which a cell maintains its position in the body, including only transient cell associations, for example, as integrin-mediated attachment.

As used herein, the term "vascular cell tumors" means any benign or neoplastic growth with an endothelial or blood vessel cellular component, including hemangiomas and sclerosing angiomas, Kaposi's sarcoma, lymphangioma, glomangiomas, i.e., glomus tumor, angiosarcoma and hemangioendotheliomas.

As used herein, the term "amplification" refers to the generation of specific DNA sequences using specific oligonucleotide primers through the use of techniques generally described as polymerase chain reaction (PCR), which are well known in the art, described for example in *PCR Technology,* Erlich, Ed., Stockton Press, New York, N.Y., (1989), and, *The Polymerase Chain Reaction,* Mullis, K. B., et al., Eds., Maple Press Co., York, Pa. (1994), both of which are incorporated herein by reference.

As used herein, the term "amino acid" refers to any synthetic or naturally occurring amino acid, including L- and D-amino acids. This includes chemically modified amino acids, amino acid analogs, naturally occurring amino acids that are not usually incorporated into proteins such as norleucine, and synthetic compounds having chemical properties known in the art to be characteristic of an amino acid, provided that the compound can be substituted within a protein such that the protein retains its biological activity. For example, glutamine can be an amino acid analog of asparagine, provided that it can be substituted without effecting biological activity. An amino acid mimetic can have a structure that exhibits substantially the same spatial arrangement of functional groups as an amino acid but does not necessarily have both the α-amino and α-carboxyl groups characteristic of an amino acid. Other examples of amino acids and amino acids analogs are listed in Gross and Meienhofer, *The Peptides: Analysis, Synthesis, Biology,* Academic Press, Inc., New York (1983), which is incorporated herein by reference.

As used herein, the term "subject" means a vertebrate, preferably a mammal and, in particular, a human.

The sFN of the invention, as defined above, comprising fibronectin, polypeptide fragments or modifications of fibronectin, or any polypeptide which when incorporated or used in generating sFN retains the biological activity of sFN, or any molecule useful in generating sFN, can be isolated or synthesized using methods well known in the art. Such methods include recombinant DNA methods and chemical synthesis methods for production of proteins. For example, recombinant fibronectin polypeptide fragments can be made in bacteria or chemically synthesized. Fibronectin, fibronectin polypeptide fragments or any polypeptide compound used in the invention can be isolated from animal tissue or plasma or produced and isolated from cell culture. They may be produced and isolated from genetically altered animals, such as transgenic animals, to generate more endogenous or exogenous forms of fibronectin. Methods that can be used in synthesizing fibronectin or fibronectin fragments or modification useful for generating sFN are well known in the art, and include those described in Example I and II below, and Morla, A., et al., supra. Sequences as in Kornblihtt, et al., *EMBO J.* 4:1755–1759 (1985), incorporated herein by reference, or, are available from Genbank, NCBI, NIH, and easily searchable, for example, on the internet. NCBI's database is herein incorporated by reference in its entirety.

sFN can be generated in vitro by treating purified fibronectin or fragments of fibronectin in solution with fibronectin-binding polypeptides containing at least one fibronectin-fibronectin binding site. These sFN-generating compounds have the property of enhancing fibronectin-fibronectin binding and fibronectin-fibronectin intermolecular associations. This enhancement of fibronectin-fibronectin binding and/or intermolecular association can generate sFN in vitro and in vivo.

The invention is not limited by which mechanism(s) may generate sFN. However, fibronectin-binding compounds appear to act by interfering with the intramolecular binding interactions that keep fibronectin in its soluble configuration. Once those interactions are disrupted, the fibronectin molecule undergoes self-assembly into fibrils. For example, sFN can be generated by incubating an sFN-generating polypeptide with fibronectin, mixing at a molar ratio of about 1:150, based on a molecular weight (MW) of 220,000 daltons for monomer fibronectin. This basic formulation or a routinely derived variation can be used in the ex vivo treatment of cells or in vivo administration (Morla, A., et al., (1994) supra). sFN-generating polypeptides can be administered intraperitoneally to generate sFN in vivo by the innoculation of, for example, a 250 uM solution of polypeptide.

Fibronectin-binding polypeptides containing at least one fibronectin-fibronectin binding site include polypeptides derived from the first type III repeat of fibronectin, designated III-1 or $III_1$, residues 578 to 673 in the human fibronectin sequence (SEQ ID NO:2), according to the numbering method of Kornblihtt, et al., supra, as shown in FIG. 1. Fibronectin-binding polypeptides also include a 14 kDa fragment (SEQ ID NO:1), the sequence of human fibronectin spanning residues 600 to 708 (Id.), and fragments of this 14 kDa polypeptide, including or $III_1$-C (SEQ ID NO:3) and $III_1$-F (SEQ ID NO:6) (previously designated as $III_1$-E in Morla, A., et al., supra), as shown in FIG. 1. Fibronectin-binding polypeptides also include the $III_1$-QE-C polypeptide (SEQ ID NO:7); and, III-10 (SEQ ID NO:8) as described by Hocking, D. C., et al., *J. of Cell Biol.* 133:431–444 (1996), which is incorporated herein by reference.

The 14 kDa polypeptide is a first type III ($III_1$) repeat unit of fibronectin. It has the following sequence of human fibronectin, which spans residues 600 to 708 (SEQ ID NO:1): NAPQPSHISK YILRWRPKNS VGRWKEATIP GHLNSYTIKG LKPGVVYEGQ LISIQQYGHQ EVTR-FDFTTT STSTPVTSNT VTGETTPFSP LVATSESVTE ITASSFVVS (SEQ ID NO:1).

The 14 kD polypeptide shares sequence with the first type III repeat unit of fibronectin. Also designated $III_1$ or III-1, it has the following sequence: SG PVEVFITETP SQPNSH-PIQW NAPQPSHISK YILRWRPKNS VGRWKEATIP GHLNSYTIKG LKPGVVYEGQ LISIQQYGHQ EVTR-FDFTTT STST (SEQ ID NO:2).

The $III_1$-C, or III-1C, polypeptide spans residues 600 to 674 in fibronectin (Kornblihtt, et al., supra) and corresponding to the first 75 residues in the 14 kDa fragment above, has the following sequence: NAPQPSHISK YILRWRPKNS VGRWKEATIP GHLNSYTIKG LKPGVVYEGQ LISIQQYGHQ EVTRFDFTTT STSTP (SEQ ID NO:3).

The III-F (SEQ ID NO: 6) polypeptide spans residues 600 to 655 in fibronectin (Id.) and corresponding to the first 56 residues in the 14 kDa fragment above, has the following sequence: NAPQPSHISK YILRWRPKNS VGRWKEATIP GHLNSYTIKG LKPGVVYEGQ LISIQQ (SEQ ID NO: 6).

The $III_1$-QE-C (SEQ ID NO:7) polypeptide, containing the $III_1$-C (SEQ ID NO:3) sequence of fibronectin and the sequence MRGS (SEQ ID NO:12) at its N-terminus and the sequence GSRSHHHHHH (SEQ ID NO:13) at its C-terminus, has the following sequence: MRGS NAPQP-SHISK YILRWRPKNS VGRWKEATIP GHLNSYTIKG LKPGVVYEGQ LISIQQYGHQ EVTRFDFTTT STSTP GSRSHHHHHH (SEQ ID NO:7). These additional amino acids are not normally found in the human fibronectin protein (Kornblihtt, et al., supra).

Other fibronectin-binding polypeptides include the fibronectin polypeptide fragments SF1 (SEQ ID NO:4) and SF2 (SEQ ID NO:5), whose amino acid sequences are: NAPQPSHISK YILRWRPKNS VGRWKEATIP G (SF1; SEQ ID NO:4); VTSNTVTGET TPFSPLVATS ESVTEIT-ASS FVVS (SF2; SEQ ID NO:5).

The III-10 polypeptide (SEQ ID NO:8) fragment of fibronectin, as described by Hocking, D. C., et al., supra, corresponding to residues 1416 to 1509 in fibronectin (Kornblihtt, et al., supra) has the following sequence: VS DVPRDLEVVA ATPTSLLISW DAPAVTVRYY RITYGETGGN SPVQEFTVPG SKSTATISGL KPGVDYTITV YAVTGRGDSP ASSKPISINY RT (SEQ ID NO:8).

The III-11-QE-C polypeptide (SEQ ID NO:15), which can be used as a negative control in experiments identifying sFN-inducing fragments, encompasses the human fibronectin residues 1,532 to 1,599 (Kornblihtt, et al., supra) and contains the same non-fibronectin sequences at the amino and carboxy termini as $III_1$-QE-C (SEQ ID NO:7).

sFN-inducing polypeptides can be produced synthetically or as recombinant polypeptides, as described in Example I. Recombinant methods of producing polypeptides through expression of a nucleic acid sequence encoding the peptide in a suitable host cell are well known in the art and are described, for example, in Sambrook, et al., *Molecular Cloning: A Laboratory Manual,* 2nd Ed, Vols 1 to 3, Cold Spring Harbor Laboratory Press, New York (1989), which is incorporated herein by reference.

Compounds used to generate sFN can be chemically synthesized, for example, by the solid phase protein synthesis method of Merrifield, et al., *J. Am. Chem. Soc.* 85:2149 (1964), which is incorporated herein by reference. Standard solution methods well known in the art also can be used to synthesize polypeptides useful in the invention, see, for example, Bodanszky, *Principles of Peptide Synthesis,* Springer-Verlag, Berlin (1984) and Bodanszky, *Peptide Chemistry,* Springer-Verlag, Berlin (1993), each of which is incorporated herein by reference. A newly synthesized polypeptide can be purified, for example, by high performance liquid chromatography (HPLC), and can be characterized using, for example, mass spectrometry or amino acid sequence analysis.

It is understood that limited modifications can be made to sFN or sFN-generating compounds without destroying biological activity. A modification can include, for example, an addition, deletion, or substitution of amino acid residues; a substitution of a compound that mimics amino acid structure or function; and addition of chemical moieties such as amino or acetyl groups. Routine assays, including any animal model known to the skilled artisan, and assays exemplified in Examples II to XI and in Morla, et al., (1994), supra, can identify useful modifications. As noted above, modified sFN retaining activity is within the scope of the term "sFN" of the present invention.

A particularly useful modification of sFN is one that confers, for example, increased stability. For example, incorporation of one or more D-amino acids or substitution or deletion of lysine can increase the stability of sFN by protecting against protein degradation. For example, D-alanine substitutions confer increased stability by protecting the protein from endoprotease degradation, as is well known in the art, see, for example, page 247 of Partridge, *Peptide Drug Delivery to the Brain,* Raven Press, New York (1991), which is incorporated herein by reference. The substitution or deletion of a lysine residue confers increased resistance to trypsin-like proteases, as is well known in the art (Partridge, supra). These substitutions increase stability and, thus, the bioavailability of sFN, but do not affect its biological activities.

A useful modification also can be one that promotes protein passage across the blood-brain barrier, such as a modification that increases lipophilicity or decreases hydrogen bonding, as described in Banks et al., *Peptides* 13:1289–1294 (1992), which is incorporated herein by reference, and Pardridge, supra. A chimeric protein-pharmaceutical that has increased biological stability or increased permeability to the blood-brain barrier, for example, also can be useful in the methods of the invention.

As used herein, the term "effective amount" means the amount of sFN or sFN-generating compound useful for ameliorating tumor metastasis, tumor growth, angiogenesis or any of the methods disclosed herein. An effective amount to be administered systemically on a daily basis depends on many factors, including for example the age, medical history and body weight of the subject. The effective amount can be determined empirically using methods well known to those in the art, including assays in primates and clinical trials in humans. While an effective amount to be administered systemically on a daily basis can be about 0.1 µg/kg body weight to about 100 mg/kg body weight, the methods of the invention are not limited by any dosage amounts or schedules.

The total effective dose can be administered to a subject as a single dose, either as a bolus or by infusion over a relatively short period of time, or can be administered using a fractionated treatment protocol, in which multiple doses are administered over a more prolonged period of time.

The sFN or sFN-generating compound can be formulated as a pharmaceutical composition suitable for use in any manner, including for example as a powder, lyophilized powder, solution, emulsion or suspension. Solid form preparations include, for example, powders, tablets, dispersible granules, capsules, cachets, and suppositories. For examples of drug formulations, see *Remington's Pharm. Sci.*, eds. Gennaro, A. R., et al., 18th Ed. (Mack Printing Co., Easton, Pa., 1990), incorporated herein by reference.

A pharmaceutically acceptable carrier of well known type can be administered with sFN. The sFN can be formulated as a pharmaceutical composition suitable for use with a variety of drug delivery systems. As used herein, the term "pharmaceutically acceptable carrier" encompasses any of the standard pharmaceutical carriers, such as a phosphate buffered saline (PBS) solution, water, and emulsions, such as an oil/water or water/oil emulsion, and various types of wetting agents. The compositions also can include stabilizers and preservatives. For examples of carriers and stabilizers see *Remington's Pharm. Sci.*, supra. Methods for drug delivery useful in the invention are reviewed in Langer, *Science* 249:1527–1533 (1990), incorporated herein by reference.

As used herein, the term "administering" encompasses any method of administration known to one skilled in the art, including but not limited to intravenously, intramuscularly, intradermally, subcutaneously, intracranially, intracerebrospinally, epidurally, topically or orally. Direct intracranial injection or injection into the cerebrospinal fluid also can be used to introduce an effective amount into the central nervous system of a subject. Administration to peripheral neural tissue can be by direct injection or local topical application or by systemic administration. sFN or a sFN-generating compound can be injected directly into the bloodstream of the subject. A typical pharmaceutical composition for intravenous infusion, for example, can be made up to contain 250 ml of sterile Ringer's solution, normal saline or PBS or sterile water and up to about 1 to 2 grams of sFN. Actual methods for preparing and formulating parenterally administrable compounds are known or apparent with only routine experimentation to those skilled in the art and are described in more detail in for example *Remington's Pharm. Sci.*, supra.

Oral administration often can be desirable, provided sFN or sFN-generating compound is modified so as to be stable to gastrointestinal degradation and readily absorbable. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

sFN or sFN-generating compound can be administered in a sustained release form. The sustained release form has the advantage of inhibiting growth, metastases, endothelial growth or the like over an extended period of time without the need for repeated administrations. Sustained release can be achieved, for example, with a sustained release material such as a wafer, an immunobead, a micropump or other material that provides for controlled slow release. Such controlled release materials are well known in the art and available from commercial sources (Alza Corp., Palo Alto Calif.; Depotech, La Jolla Calif.; see, also, Pardoll, *Ann. Rev. Immunol.* 13:399–415 (1995), which is incorporated herein by reference). In addition, a bioerodible or biodegradable material that can be formulated with sFN or sFN-generating compound, such as polylactic acid, polygalactic acid, regenerated collagen, multilamellar liposomes or other conventional depot formulations, can be implanted to slowly release sFN or sFN-generating compound. The use of infusion pumps, matrix entrapment systems, and transdermal delivery devices also are contemplated in the present invention.

sFN or sFN-generating compound also can be advantageously enclosed in micelles or liposomes. Liposome encapsulation technology is well known. Liposomes can be targeted to a specific tissue, such as neural tissue, through the use of receptors, ligands or antibodies capable of binding the targeted tissue. The technology and preparation of such formulations is well known in the art, see, for example, Pardridge, supra, 1991; Radin, et al., *Meth. Enzymol.* 98:613–618 (1983) and Nabel, G. J., et al., *Proc. Natl. Acad. Sci. USA* 90:11307–11311 (1993), which are incorporated herein by reference.

The invention also provides for methods in which sFN or sFN-generating polypeptides are generated in vivo. These methods include implanting into the subject a cell genetically modified to express and secrete sFN or polypeptides capable of generating sFN in vivo. They also include gene therapy involving inserting into the subject genes capable of expressing sFN-generating polypeptides. These methods can provide a continuous source of sFN or sFN-generating polypeptides. For a subject suffering from a long-term risk of metastasis or tumor recurrence, such methods have the advantage of obviating or reducing the need for repeated administration.

For ex vivo gene transfer, using methods well known in the art, a cell can be transiently or stably transfected with an expression vector containing the desired nucleic acid sequences, for example as described in Chang, *Somatic Gene Therapy*, CRC Press, Boca Raton (1995), which is incorporated herein by reference. The transfected cell is then implanted into the subject. Methods of transfecting cells ex vivo are well known in the art, for example, Kriegler, *Gene Transfer and Expression: A Laboratory Manual*, W. H. Freeman & Co., New York (1990), incorporated herein by reference. For the transfection of a cell that continues to divide such as a fibroblast, muscle cell, glial cell or neuronal precursor cell, retroviral or adenoviral vectors can be used. For the transfection of an nucleic acid into a postmitotic cell such as a neuron, for example, a replication defective herpes simplex virus type 1 or Sindbis virus vector can be used, and such methods are well known in the art, as in During, et al., *Soc. Neurosci. Abstr.* 17:140 (1991); Sable, et al., *Soc. Neurosci. Abstr.* 17:570 (1991); Dubensky, T. W., et al., *J. of Virology* 70:508–519 (1996); each incorporated herein by reference.

For in vivo gene therapy, using methods well known in the art, the desired cell or tissue can be transiently or stably transfected with an expression vector containing the desired nucleic acid sequence(s) to effect expression of the sFN-generating compound or secretion of sFN, for example, as described in Acsadi, G., et al., *New Biol.* 3:71–81 (1991); Chang, supra; Chen, S., et al., *Proc. Natl., Acad. Sci. USA* 91:3054–3057 (1994); Culver, K. W., et al., *Science* 256:1550–1552 (1992); Furth, P. A., et al., *Molec. Biotech.* 4:121–127 (1995); which are incorporated herein by reference.

sFN Inhibits Primary Tumor Implantation In Vivo

Example III discloses the inhibitory effect of sFN on the efficiency of tumor implantation. An experimental mouse model was used. Murine experimental models are well recognized in the art as models for studying tumorigenesis and metastasis and are recognized in the art as predictive of the success of anti-metastatic pharmaceutical agents. See for example: Mu, J., et al., *Cancer Res.* 55:4404–4408 (1995); Berlin, O., et al., *Cancer Res.* 53:4890–4898 (1993); Welch, D. R., et al., *Int. J. Cancer* 47:227–237 (1991); Kumagai, H., et al., BBRC 177:74 (1991); Komazawa, H., et al., *Carbohydrate Polymers* 21:299–307 (1993); Brodt, P., *Cancer Res.* 46:2442–2448 (1986); Samid, D., et al., *Clinical Biotech.* 1:21 (1989); Dubois-Stringfellow, N., et al., *Am J. Pathol.* 144(4):796–806 (1994), all incorporated herein by reference.

Human tumorigenic cells were pre-incubated with sFN or various control treatments and injected subcutaneously into mice. The experimental results disclosed in Example III, FIG. 2, demonstrate that ex vivo sFN pretreatment inhibits local growth of tumor cells, specifically, the growth of sFN pre-treated and subcutaneously inoculated C8161 melanoma and KRIB osteosarcoma cells. This example demonstrates that tumor cell exposure to sFN inhibits disseminated tumor formation and inhibits the tumor's ability to grow and form metastases.

Exposure to sFN Inhibits Implantation of Intravenously Circulating Tumor Cells

Using an experimental metastasis model, Example IV discloses the inhibitory effect of sFN on circulating primary tumor cells. Exposure of intravenously circulating tumor cells to sFN inhibits their ability to form disseminated tumor foci.

In order to determine the effect of sFN on experimental metastasis, human tumorigenic cells were pre-incubated with sFN or various control treatments for 10 minutes, and injected intravenously into mice. The experimental results disclosed in Example IV, FIG. 3, demonstrate that exposure of circulating tumor cells to sFN inhibits tumor cell metastasis. Specifically, these experiments show that ex vivo pretreatment with sFN inhibits metastasis of intravenously administered Krib osteosarcoma, C8161 melanoma and HT-29 carcinoma to both the lungs and lymphoid nodes.

Intraperitoneally Administered sFN Inhibits Experimental and Spontaneous Metastasis from Established Solid Tumors Example V discloses the inhibitory effect of intraperitoneally injected sFN on experimental and spontaneous metastases from established solid tumors. As FIG. 4A demonstrates, intraperitoneally injected sFN causes a specific and significant decrease in the number of lung metastatic foci resulting from circulating osteosarcoma and melanoma tumor cells.

Figures 1, 4A:
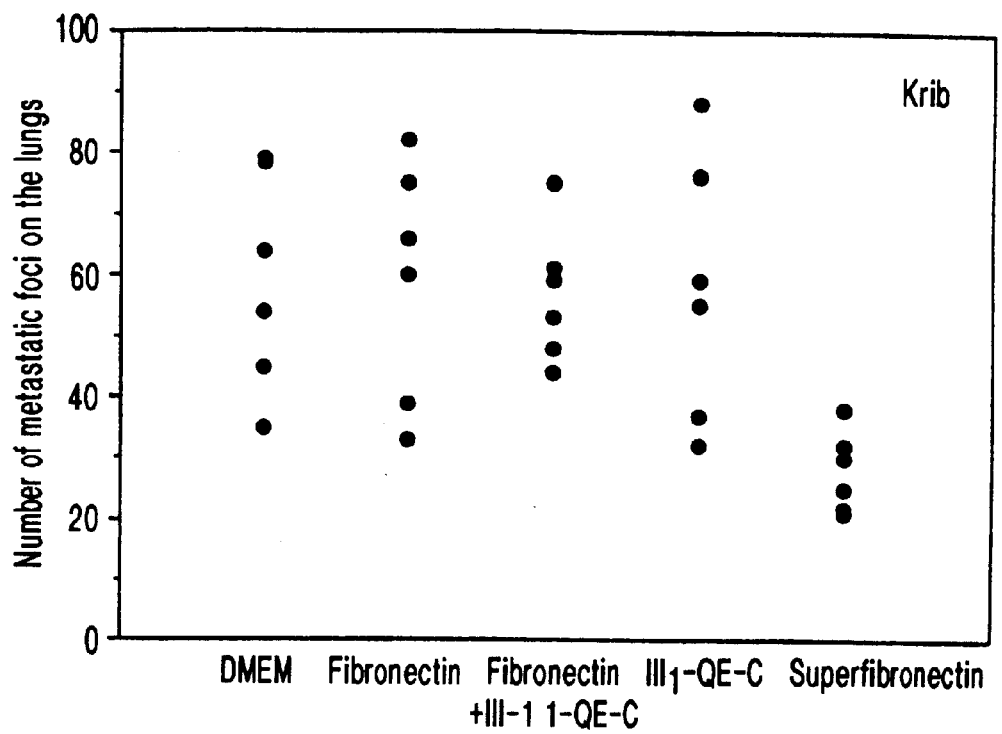
Figures 2, 4A:
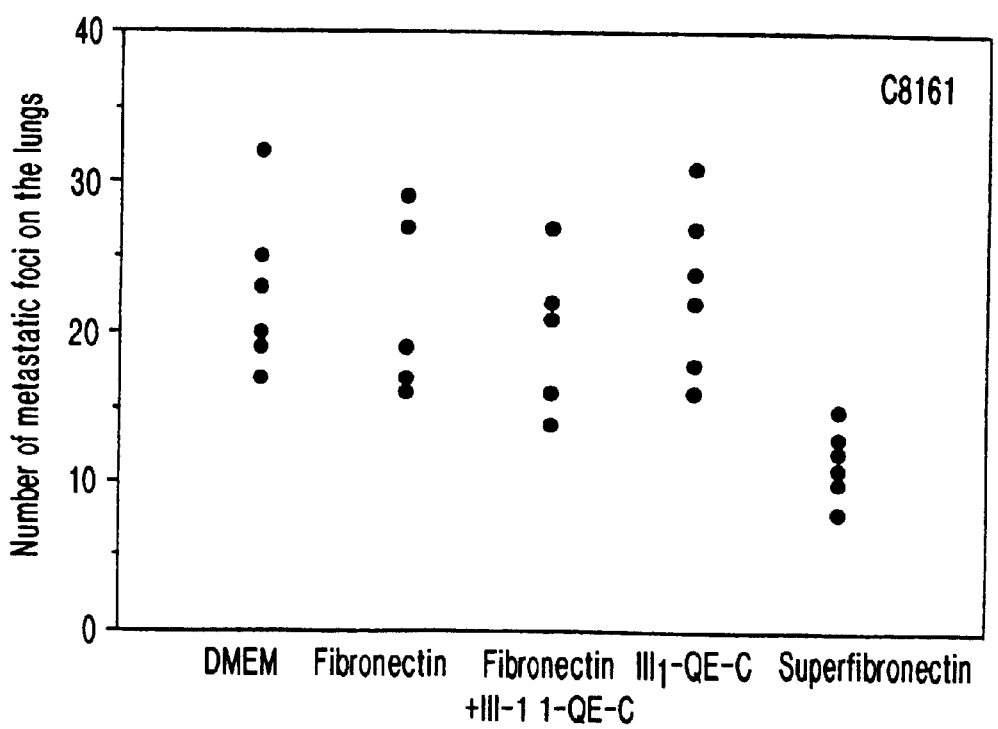
Figures 1, 4B:
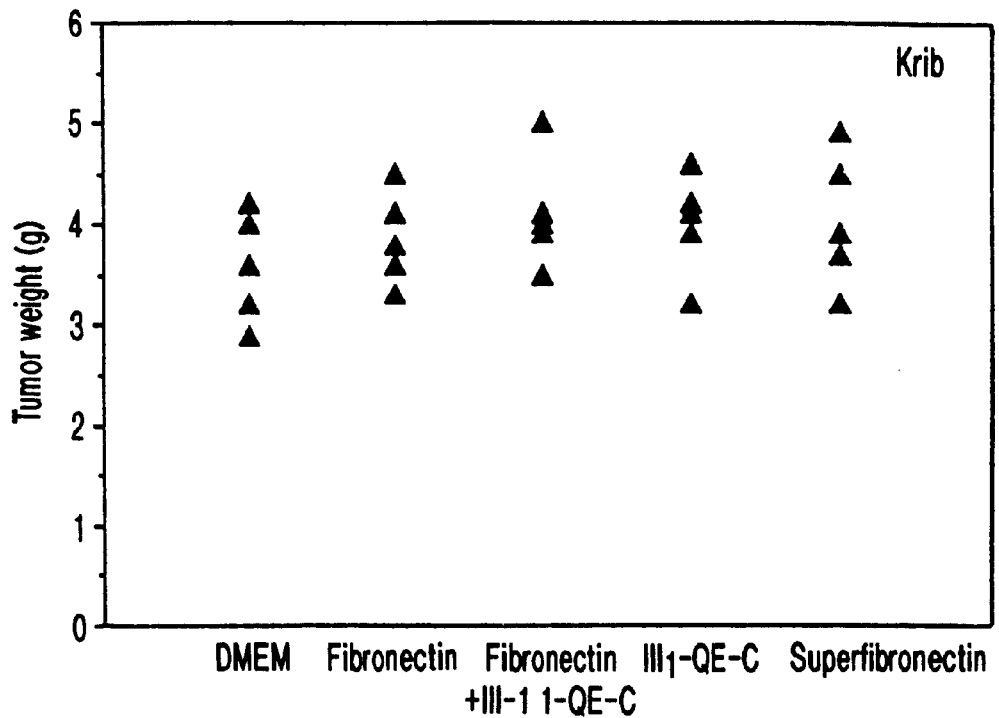
Figures 2, 4B:
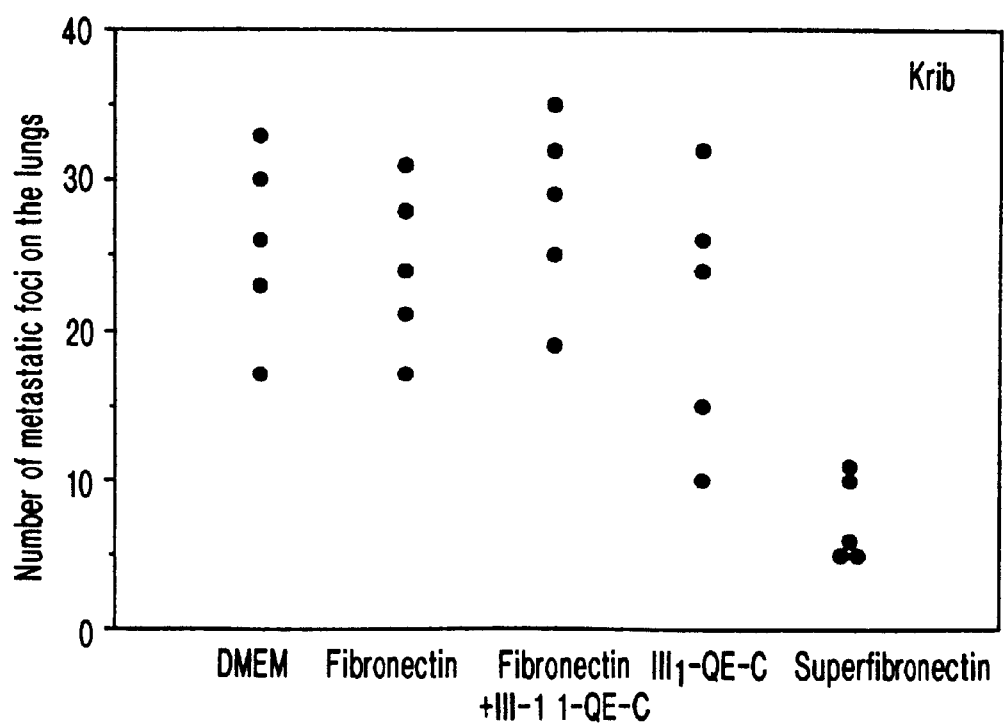
Figures 1, 4C:
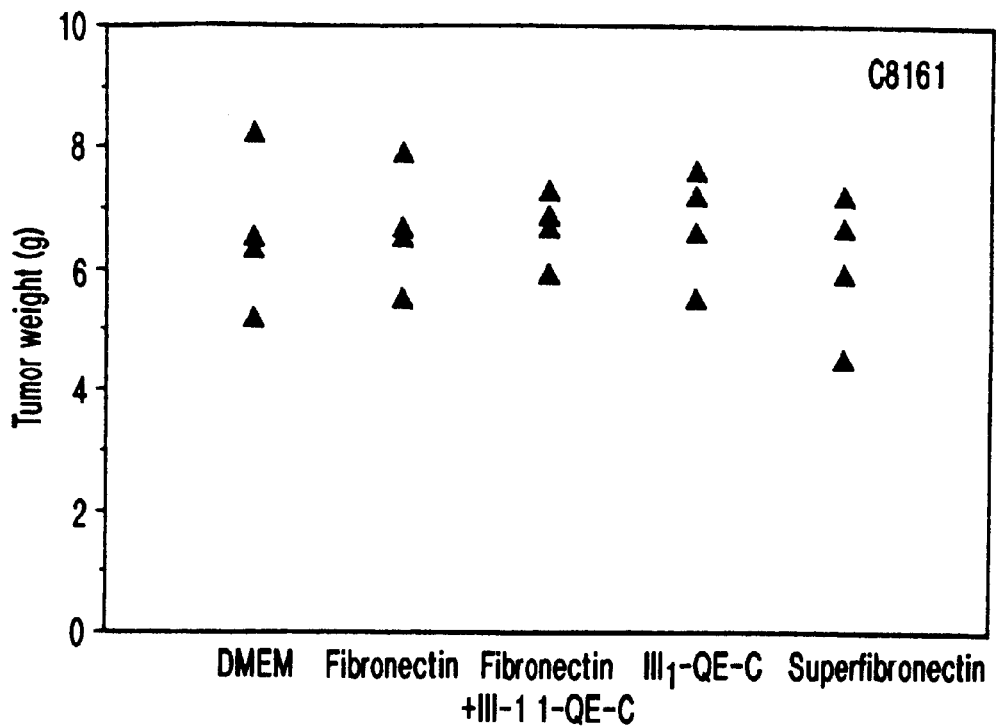
Figures 2, 4C:
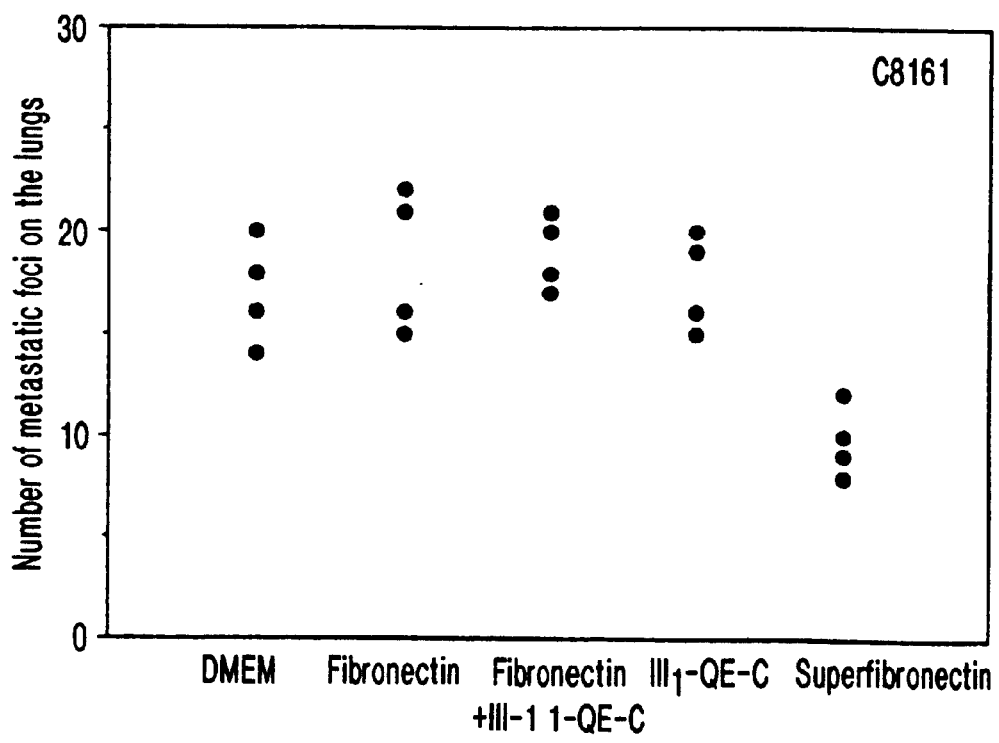

FIGS. 4B and 4C demonstrate that intraperitoneally administered sFN also inhibits spontaneous metastasis from pre-established tumors, specifically, osteosarcoma and melanoma subcutaneous tumors. Mice were inoculated with untreated tumor cells subcutaneously, the tumors were allowed to grow to about 6 mm in diameter, and the mice were then treated with intraperitoneal sFN or control injections. The sFN-treated mice showed significantly less metastatic growth in the lungs than the control mice.

These experimental results demonstrate that intraperitoneally injected sFN inhibits spontaneous metastasis from established solid tumors and experimental metastasis from circulating tumor cells. Specifically, the above experiments show that systemically administered sFN treatment inhibits spontaneous metastasis from established melanoma and osteosarcoma solid tumors.

Superfibronectin is Effective in Reducing the Spread of Tumors within the Peritoneal Cavity Example VI discloses that sFN is effective in reducing the spread of tumors within the peritoneal cavity. A series of experiments carried out with an ovarian cancer model, as demonstrated in FIG. 5, indicates that sFN is effective in reducing the number of metastatic ovarian carcinoma cell-derived foci on the peritoneal wall, associated with the intestines and associated with the ovaries.

Superfibronectin and the Fibronectin Fragment III-1C Cause Regression of Established Primary Tumor In Vivo Example VII discloses that sFN can cause the regression of established primary tumors in vivo. As demonstrated in FIG. 6, sFN or the sFN-generating fragment $III_1$-QE-C (SEQ ID NO:7), which is a variant of $III_1$-C (SEQ ID NO:3), can cause the regression of an established hemangioma, a tumor of endothelial cell origin, and breast carcinoma tumors. This result demonstrates that the anti-tumor effect of sFN is not limited to inhibition of metastasis, but also includes its ability to cause regression of established primary tumors, specifically, that sFN can suppress the growth and causes regression of endothelially derived tumors and breast carcinoma tumors.

These data also demonstrate that the invention provides a method of suppressing the growth of tumors using sFN-generating compounds. Administration of $III_1$-QE-C (SEQ ID NO:7) suppresses the growth and causes regression of endothelially derived breast carcinoma tumors. Specifically, sFN and the sFN-generating recombinant peptide $III_1$-QE-C (SEQ ID NO:7) are demonstrated to cause regression of Bend hemangiomas and MDA-MB-435 breast carcinoma tumors upon peritumoral injection. Additionally, FIG. 6 shows that ex vivo pretreatment of these tumor cells with sFN or the sFN-generating recombinant peptide $III_1$-QE-C (SEQ ID NO:7) also can inhibit tumor growth.

sFN Interferes with Cell Spreading and Migration

Example VIII, to demonstrate mechanisms that contribute to the biological effects of sFN, including the inhibitory effect of sFN on metastasis, discloses the effect of sFN on tumor cell spreading and migration. FIG. 7 demonstrates that sFN suppresses tumor cell spreading and cell migration. After preincubation with sFN, tumor cells were unable to spread on any of the immobilized human extracellular matrix proteins fibronectin, laminin, collagen IV, and vitronectin or on BSA. sFN inhibited the migration of the osteosarcoma and melanoma tumor cells on fibronectin, vitronectin, type IV collagen, and laminin, by about 70%.

sFN is Significantly Superior to Intergrin Binding Peptides in the Inhibition of Metastases Example IX demonstrates that tumor cell exposure to sFN is significantly more efficient in inhibiting tumor metastasis than integrin-binding peptides, such as RGD-containing peptides. The literature has observed that inhibition of tumorigenicity and metastasis may be seen upon selective blocking of some types of integrins by RGD-containing peptides which mimic the ligand binding sites of those integrins. However, as the data in FIG. 8 demonstrates, sFN is significantly superior to such RGD-containing peptides in its ability to inhibit tumor cell metastasis.

sFN Inhibits Cytokine-Induced Endothelial Cell Growth and Cytokine-Induced Angiogenesis The experimental results disclosed in Example X, FIG. 9, demonstrates that the biological activity of sFN is not limited to inhibition of metastasis or tumor growth, but also includes an ability to inhibit endothelial cell growth and cytokine-induced angiogenesis not associated with any tumorigenic or metastatic process.

sFN Injected Intraperitoneally Reaches the Circulation

The experimental results disclosed in Example XI, FIG. 10, demonstrate that sFN injected intraperitoneally reaches the circulation. The effectiveness of intraperitoneally administered sFN in reducing distal metastases, such as lung colonization, from established subcutaneous tumors suggested that sFN was absorbed and redistributed systemically from the peritoneal cavity. As shown in FIG. 10, radioactive material consistent in size with sFN was detected in the blood 15 minutes after the injection and reached peak levels after 2 hours.

Administration of sFN to Patients to Inhibit the Formation of Tumor Metastases

Example XII discloses a protocol for administering sFN or a sFN-generating compound to a subject with diagnosed primary tumor for the purpose of inhibiting metastasis from primary tumors.

The following examples are intended to illustrate but not limit the present invention.

EXAMPLE I

Isolation and Synthesis of Fibronectin and Fibronectin Fragments

Materials

The materials used in all of the following examples include the following: Alpha-Minimal Essential Medium (α-MEM) (Gibco Laboratories, Grand Island, N.Y.); fetal calf serum (FCS) (Tissue Culture Biologicals Tulare, Calif.); Glutamine Pen-Strep (Irvine Scientific, Santa Ana, Calif.); IMMUNOLON 2 REMOVAWELL™ strips (Dynatech Laboratories, Chantilly, Va.); IODO-GEN™ (Pierce, Rockford, Ill.); CNBr-activated Sepharose, heparin-Sepharose, gelatin-Sepharose, Sepharose CL-4B, S-Sepharose, NAP-25 columns, plasmid vector pGEX-2T (Pharmacia LKB, Piscataway, N.J.); precast SDS-PAGE gels (BioRad, Richmond, Calif., and Novex, San Diego, Calif.); IMMOBILON™ nylon transfer membrane (Millipore, Bedford, Mass.); vent DNA polymerase (New England Biolabs, Inc., Beverly, Mass.); LAB-TEK™ 8-well Chamber Slides (Nunc, Naperville, Ill.); HPLC columns (Vydac, Hesperia, Calif.); and, collagen type I (Collaborative Research, Bedford, Mass.). All other reagents were acquired from Sigma, St. Louis, Mo. Human plasma fibronectin is commercially available, and was obtained from the Blood Transfusion Service of the Finnish Red Cross in Helsinki, Finland.

Isolation of Fibronectin Fragments

Fibronectin was digested with α-chymotrypsin (0.1% by weight, TLCK treated) for 4 hours at 25° C. The digestion was stopped by adding phenylmethylsulphonyl fluoride (PMSF), 20 µg/ml final concentration. The preparation was passed over a gelatin-Sepharose column according to Engvall and Ruoslahti, *Int. J. Cancer* 20:1 (1977). After washing the gelatin-Sepharose column with 50 mM Tris-HCl, pH 7.5, gelatin-bound material was eluted with 4 M urea, 50 mM Tris-HCl, pH 7.5, followed by extensive dialysis against distilled water and lyophilization. The material bound to gelatin-Sepharose consists primarily, over 98%, of fragments of 40 kDa and 45 kDa size. The 40 kDa and 45 kDa fragments do not contain the $III_1$ region (SEQ ID NO:2) and are useful as negative controls in experiments characterizing polypeptides containing fibronectin binding sites.

The flow-through from the gelatin-Sepharose column was collected and passed over a heparin-Sepharose column. The heparin-Sepharose column was washed with 50 mM Tris-HCl, pH 7.5, then heparin-bound fibronectin fragments was eluted with 1 M NaCl, 50 mM Tris-HCl, pH 7.5, then dialyzed against distilled water and lyophilized. The 14 kDa polypeptide (SEQ ID NO:1) was purified from heparin-binding fragments by reverse phase HPLC on a C-4 column. After applying heparin-binding fragments to the HPLC column in 0.06% trifluoroacetic acid, the column is eluted with a linear gradient of 0 to 60% acetonitrile in 0.06% trifluoroacetic acid. The 14 kDa fragment (SEQ ID NO:1) eluted in the 45% acetonitrile fractions.

Fibronectin was digested with cathepsin-D as described by McKeown-Longo et al., *J. Cell Biol.* 100, 364 (1985). To remove polypeptide fragments containing the gelatin-binding domain, the digested fibronectin was applied to a gelatin-Sepharose column according to Engvall and Ruoslahti (1977), supra. The unbound fraction from the gelatin-Sepharose was fractionated further on peptide columns as described in Morla, et al., *J. Cell. Biol.* 118, 421 (1992). Amino-terminal sequence analysis of isolated fibronectin fragments was done by transferring the proteins from a gel onto an IMMOBILON™ nylon membrane. The bands of interest were cut out of the membrane and microsequenced.

Synthesis of Polypeptides SF1 and SF2

Polypeptides representing various regions of the 14 kDa polypeptide (SEQ ID NO:1) were synthesized. These polypeptides can be purified by reverse phase HPLC. Polypeptide SF1 (SEQ ID NO:4) represents the region from amino acids 600 to 630 of the mature fibronectin protein (as above, according to the numbering method of Kornblihtt, et al., supra.). Polypeptide SF2 (SEQ ID NO:5) represents the region from amino acids 675 to 708 of the mature fibronectin protein (Id.).

Production of Polypeptides from the First Type III Repeat of Fibronectin: $III_1$-C, $III_1$-F, $III_1$-OE-C Polypeptides representing different regions of fibronectin were produced by PCR cloning of the region from the corresponding sequence of human fibronectin. For example, recombinant polypeptides representing the first type III repeat of fibronectin, $III_1$ (SEQ ID NO:2) were produced by PCR cloning of the region in the sequence of human fibronectin spanning residues 600 to 655 for the $III_1$-F protein (SEQ ID NO:6), and the region spanning residues 600–674 for the $III_1$-C protein (SEQ ID NO:3) (Kornblihtt, et al., (1985), supra). Fibronectin polypeptides fragments were cloned from a human placental cDNA library using methods well known in the art.

PCR primers used to synthesize the cDNA for the $III_1$-F protein (SEQ ID NO:6) were:

5'-primer,
5'-CCGGATCCAATGCACCACAGCCATCTC-3' (SEQ ID NO:9);

3'-primer,
5'-CCGGATCCCTGCTGGATGCTGATGAGC-3' (SEQ ID NO:10).

PCR primers used to synthesize the cDNA for the $III_1$-C protein (SEQ ID NO:3) were:

5'-primer,
5'-CCGGATCCAATGCACCACAGCCATCTC-3'(SEQ ID NO:9), (the same 5'-primer used for synthesizing $III_1$-F cDNA (SEQ ID NO:6));

3'-primer,
5'-CCGGATCCAGGTGTGCTGGTGCTGGTGG-3'(SEQ ID NO:11).

These primers were designed with Bam HI sites flanking the fibronectin-coding sequences to enable splicing of the fibronectin sequence in-frame either with the glutathione-S-transferase coding sequence in a pGEX-2T vector (Pharmacia LKB Biotechnology, Inc., Piscataway, N.J.,), or with the coding sequence in a pQE-12 vector (Qiagen Inc., Chatsworth, Calif.).

The PCR reactions were performed using Vent DNA polymerase according to the manufacturer's recommendations, and with the following temperatures and times: 94° C., 1 min; 50° C., 2 min., and 74° C., 2 min., for 30 cycles. The PCR products were purified on agarose gel, digested with Bam HI, purified again on an agarose gel, then ligated into Bam HI-digested and phosphatase-treated pGEX-2T and pQE-12, respectively. M15pREP4 bacteria (Qiagen Inc., Chatsworth, Calif.) were transformed with the pQE-12 plasmid and XL-1 blue bacteria (Stratagene, La Jolla, Calif.) were transformed with the pGEX-2T plasmid and clones with the appropriate expression products were isolated. When the XL-1 cells were transformed with the pGEX-2T plasmid, $III_1$-C (SEQ ID NO:3) and $III_1$-F (SEQ ID NO:6) were expressed as fusion proteins with the bacterial glutathione-S-transferase (GST) protein, as in Gearing, D. P., et al., *Bio/Technology* 7, 1157–61 (1989).

For the expression of the $III_1$-C polypeptide (SEQ ID NO:3) in the form of its variant $III_1$-QE-C (SEQ ID NO:7), a clone with the appropriate expression product was isolated, and synthesis of the polypeptide was induced by growing the culture in L-broth plus 50 μg/ml ampicillin, 50 μg/ml kanamycin, 2 mM IPTG for 5 hours at 37° C. with agitation. Cells were collected and lysed in 6 M guanidine HCl, 0.1 M $NaH_2PO_4$, 0.01 M Tris, pH 8.0. The $III_1$-QE-C protein (SEQ ID NO:7) was purified by affinity chromatography on a Nickel NTA-agarose column (Qiagen Inc., Chatsworth, Calif.). The column was washed with 8 M urea, 0.1 M $NaH_2PO_4$, 0.01 M Tris, pH 8.0. The $III_1$-QE-C polypeptide (SEQ ID NO:7) was then removed from the column with 8 M urea, 0.1 M $NaH_2PO_4$, 0.01 M Tris, pH 4.5. The purified polypeptide was dialyzed against PBS to remove the urea buffer. The final $III_1$-QE-C polypeptide (SEQ ID NO:7) preparation was greater than 95% pure as judged by SDS-PAGE and staining with Coomassie blue.

To prepare the GST fusion proteins, a clone with the appropriate expression product was isolated, and synthesis of polypeptides was induced by growing the cultures in L-broth plus 50 μg/ml ampicillin, 1.0 mM IPTG for 18 hours at 37° C. with agitation. Cells were collected and lysed, and the GST-protein expression products were purified by affinity chromatography on glutathione-agarose as described in Gearing, et al. supra. The polypeptide fragment was cleaved away from its fusion partner by thrombin digestion according to Smith et al., *Gene* 67, 31 (1988). The reaction was carried out in 50 mM Tris-HCl, pH 7.5, 150 mM NaCl, 2.5 mM $CaCl_2$ at 37° C. for 12 hours. The digest was applied to an S-Sepharose column and the fusion protein was purified from digestion products by elution with an NaCl gradient of 0 to 0.4M NaCl in 20 mM Tris-HCL, pH 6.8. The final polypeptide preparations were greater than 95% pure as judged by SDS-PAGE and staining with Coomassie blue. The resulting proteins contain 2 amino acids, glycine and serine (GS), at the amino terminus and 8 amino acids (GSPGIHRD) (SEQ ID NO:14) at the carboxy terminus which are not normally found in human fibronectin (Kornblihtt, et al., (1985), supra).

This example is illustrative of means by which the skilled artisan, using only routine experimentation, can prepare and identify other polypeptides which can be used to generate sFN in vivo or in vitro.

EXAMPLE II

Synthesis, Isolation and Preparation of Superfibronectin (sFN)

sFN was generated by incubating the recombinant polypeptide III1-QE-C (SEQ ID NO:7) and fibronectin, mixing at a molar ratio of about 1:150, based on a molecular weight (MW) of 220,000 daltons for monomer fibronectin. 100 μg of fibronectin was mixed with 100 μl of the recombinant polypeptide fragment at 500 μM. For producing sFN for intraperitoneal (IP) administration, fibronectin was mixed with the recombinant polypeptide at a molar ratio of about 1:50, based on a MW of 220,000 daltons for monomer fibronectin. 100 μg of fibronectin was incubated with 30 μl of $III_1$-QE-C (SEQ ID NO:7) at 500 μM and mixed for about 10 minutes at room temperature. The resultant polymeric fibronectin, or sFN, resulting from this $III_1$-QE-C (SEQ ID NO:7) treatment of fibronectin was ten-fold more adhesive to cells than fibronectin insolubilized directly from solution.

EXAMPLE III sFN Inhibits Primary Tumor Implantation

Tumor cells treated with sFN are inhibited from forming primary tumors when implanted subcutaneously. In order to demonstrate this inhibitory effect of sFN on the efficiency of tumor implantation, an experimental nude mouse model was used. Human tumorigenic cells were pre-incubated with sFN or various control treatments for 10 minutes and then injected subcutaneously into mice.

The human tumor cells used in experiments include: C8161 melanoma (Welch D.R., et al., *Int. J. Cancer* 47:227–237 (1991)), KRIB osteosarcoma (Berlin, O, et al., *Cancer Res.* 53:4890–4895 (1993)), and HT-29 colon carcinoma (Fogh, J., et al., *J. Natl. Cancer Inst.* 59:221–226 (1977)). Cells were cultured in Dulbecco's modified Eagle's medium (DMEM), 10% FCS with sodium pyruvate, L-glutamine and penicillin/ streptomycin (Gibco BRL, Bethesda, Md.), and were in continuous culture for less than three consecutive passages prior to all experiments. Culture medium was changed 12 hours before cells were injected into mice. Cells were detached with PBS containing 2.5 mM EDTA from monolayers that had reached approximately 80% confluence, washed three times with DMEM, counted and resuspended in DMEM. Cell viability was monitored before and after ex vivo treatments by using Trypan Blue exclusion and MTT (3-[4,5-dimethylthazol-2-yl]-2,5-diphenytetrazolium bromide) assays, as described in Tada, H., et al., *Eur. J. Immunol.* 93:157–165 (1986). Because sFN treated cells tended to stain blue regardless of their viability status due to the accumulation of sFN fibers on their surface, the cells were treated with trypsin 0.05% /1 mM EDTA in PBS for 5 minutes before viability evaluation by Trypan Blue exclusion.

Female Balb/c nude mice, two months old (Harlan Sprague Dawley, San Diego, Calif.) were used in all experiments. The animals were cared for according to the respective Institute's Animal Facility guidelines. Avertin (0.015 ml/g) was used as anesthetic; decomposition of the anesthetic was prevented by storing it at 4° C. in the dark for no longer than six months.

Figure 2A:
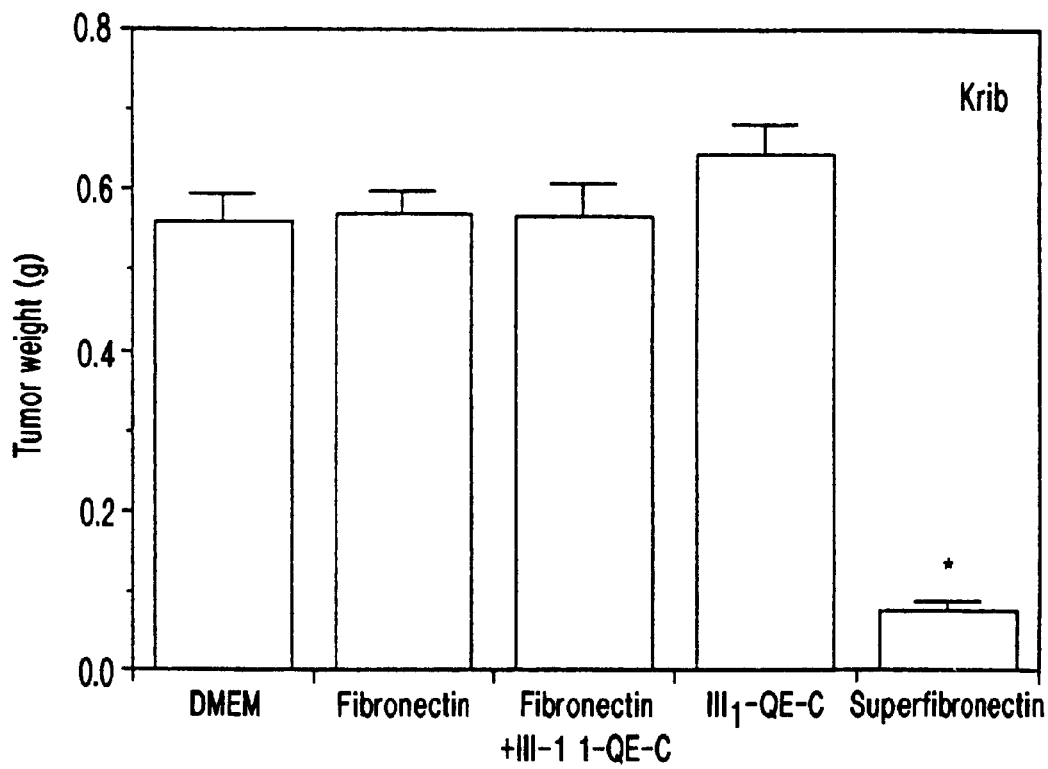
FIGS. 2A and 2B demonstrate that exposure of tumor cells to sFN inhibits their local growth in vivo, and specifically, that ex vivo sFN pretreatment of tumor cells inhibits the growth of subcutaneously inoculated melanoma and osteosarcoma cells.
Figure 2B:
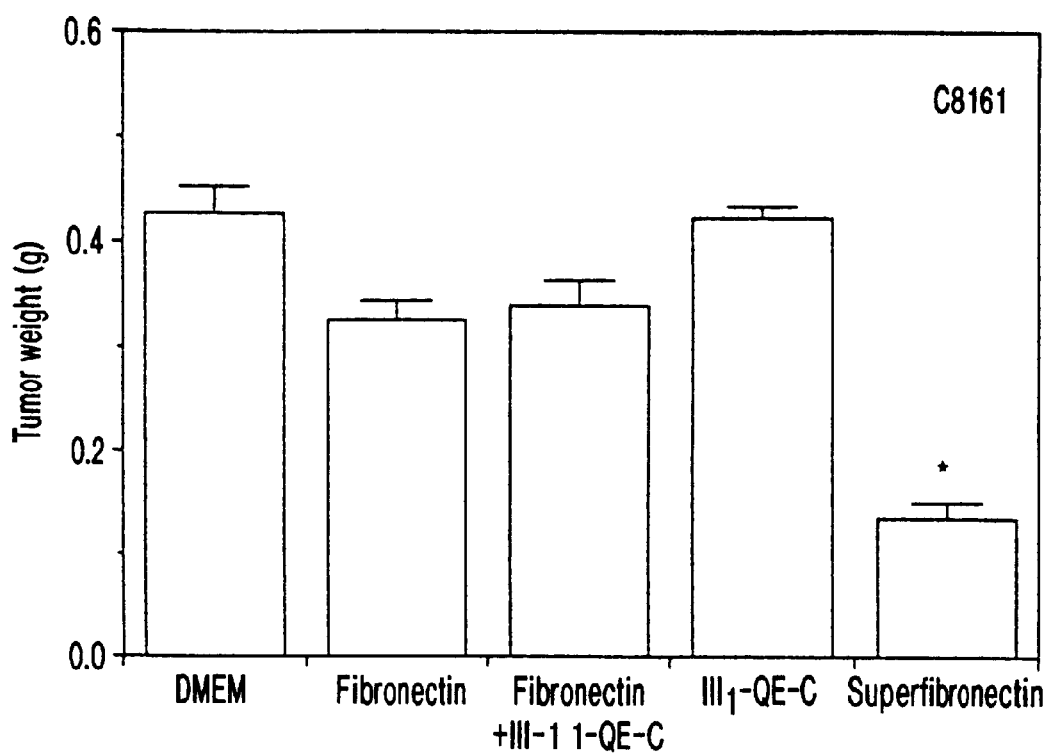

As shown in FIGS. 2A and 2B, tumor cells were pre-treated for 10 minutes with media alone (DMEM), fibronectin alone, fibronectin plus III-11-QE-C (SEQ ID NO:15), $III_1$-QE-C (SEQ ID NO:7) alone, or sFN. As in all tumor implantation experiments, cells were pre-incubated for 10 minutes at room temperature, and then inoculated subcutaneously ($10^6$cells/200 μl) on the left flank of the mice (6 animals per group). The order of injections was randomized to eliminate any differences in incubation time that might bias the outcome. The treated cells were injected in two independent series.

Figures 1, 3A:
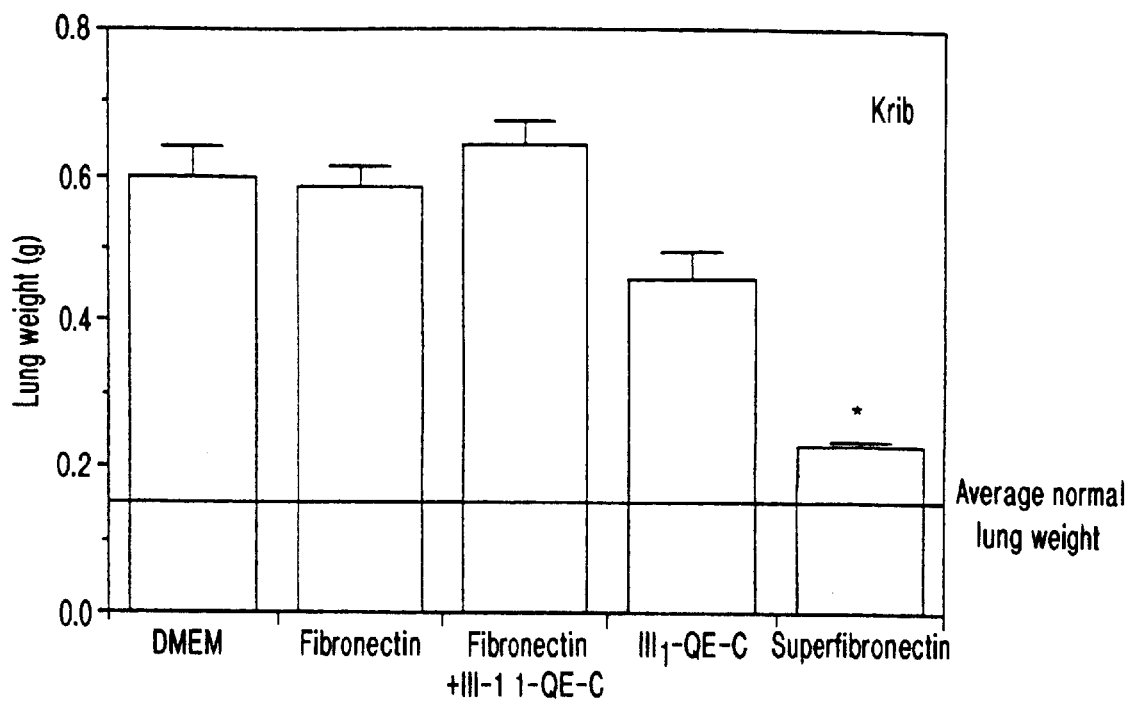
Figures 2, 3A:
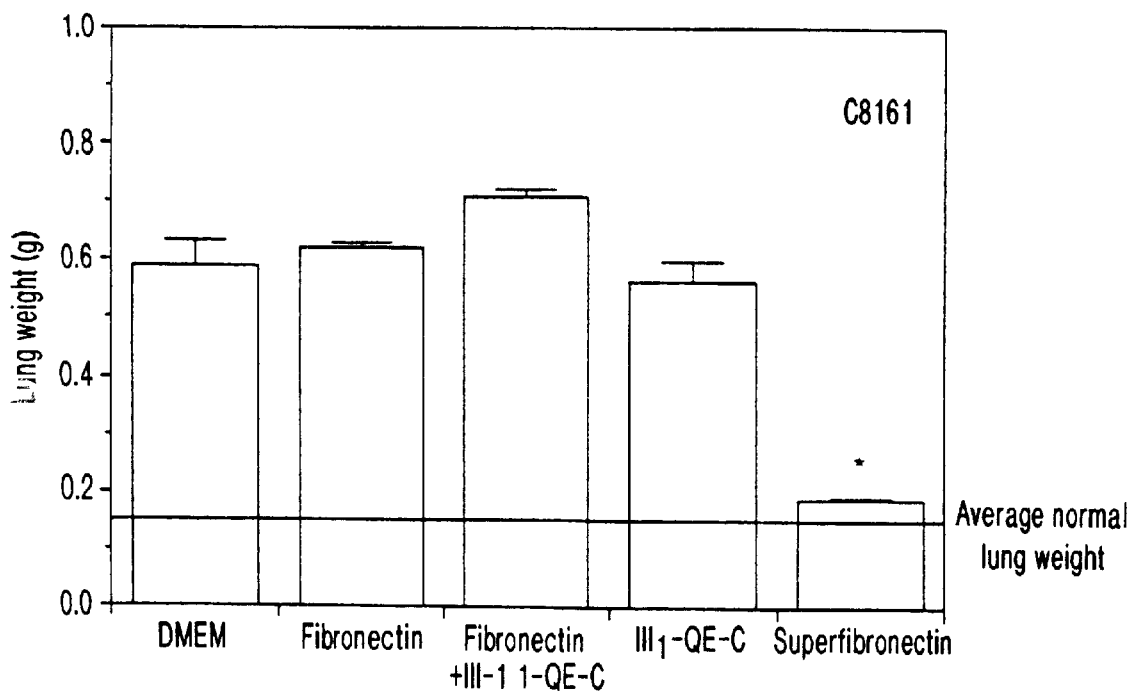
Figures 1, 3B:
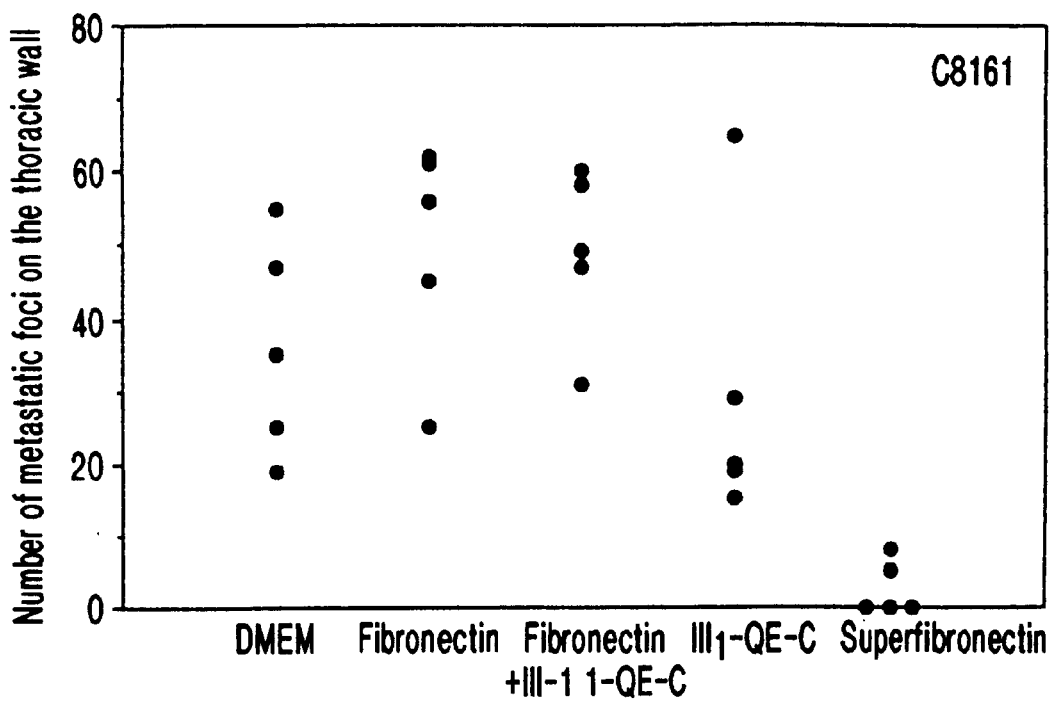
Figures 2, 3B:
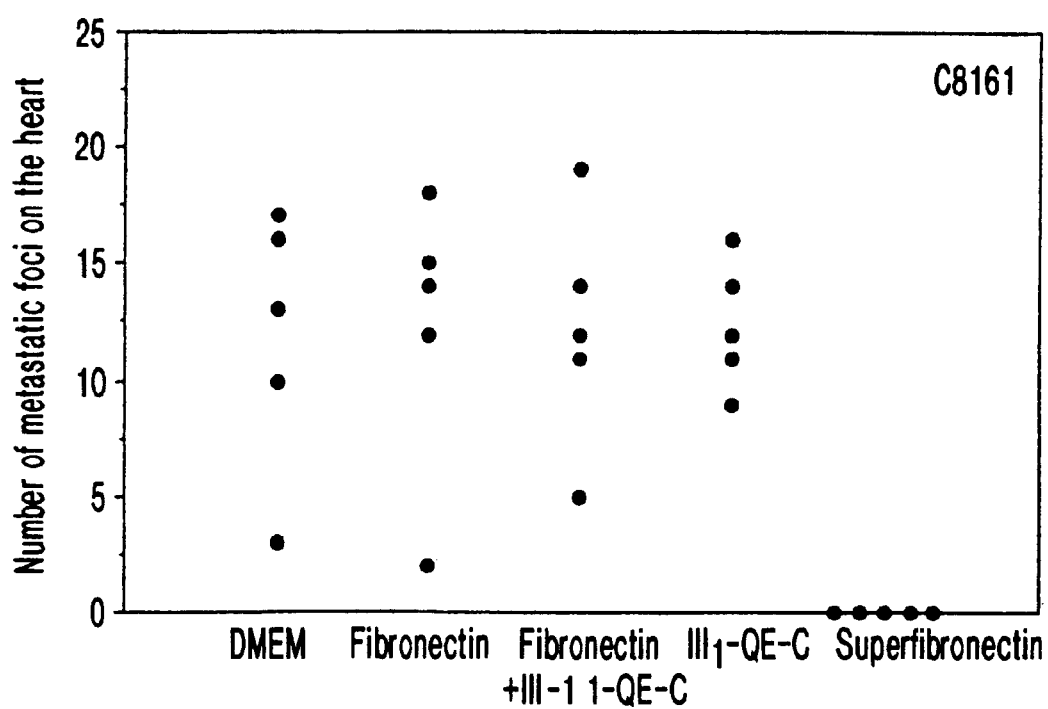
Figures 1, 3C:
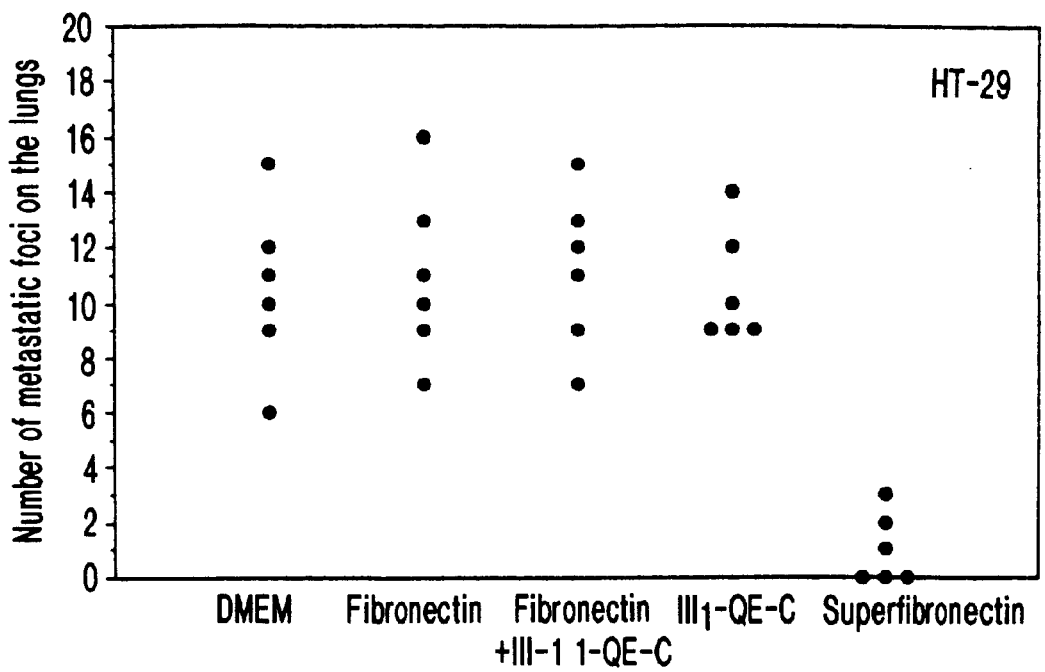
Figures 2, 3C:
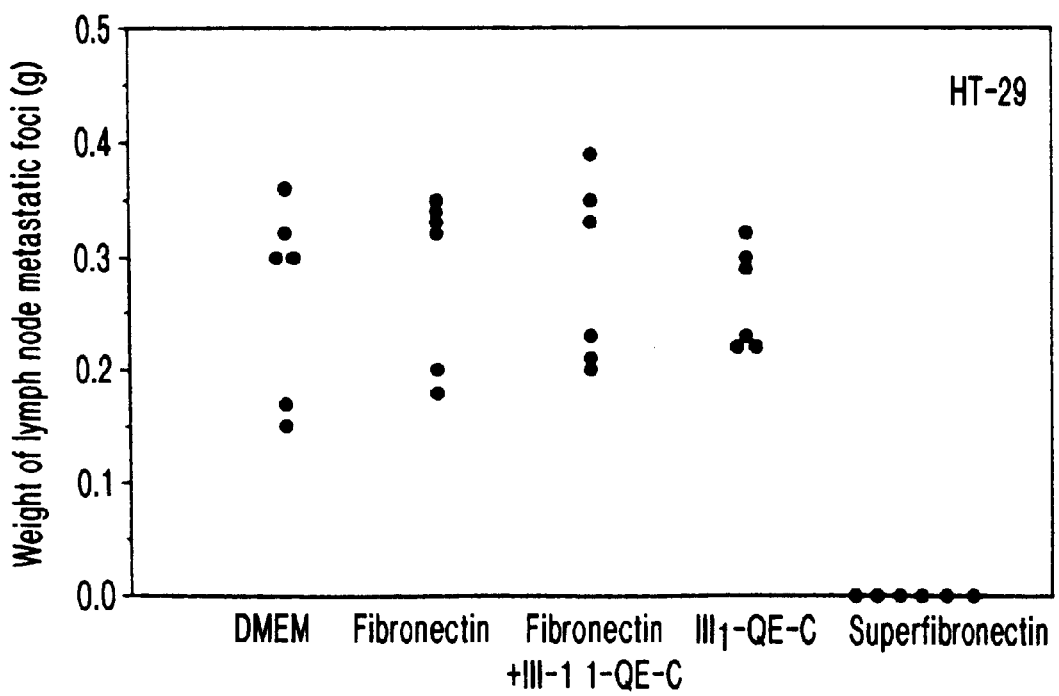

Tumor growth was monitored daily. When the tumors in the control groups reached about 0.8 gram for KRIB osteosarcoma tumors, and 0.5 gram for C8161 melanoma tumors, the animals were sacrificed and tumors were removed and weighed. In FIG. 2A, mean tumor weights in grams are 0.560, 0.571, 0.568, 0.643, and 0.174, for DMEM, fibronectin, fibronectin plus III-11-QE-C (SEQ ID NO:15), $III_1$-QE-C (SEQ ID NO:7), or sFN, respectively. In FIG. 2B, mean tumor weights in grams are 0.428, 0.325, 0.340, 0.421, and 0.186, for DMEM, fibronectin, fibronectin plus III-11-QE-C (SEQ ID NO:15), III1-QE-C (SEQ ID NO:7), or sFN, respectively. Standard error bars are also shown in FIG. 2. Unpaired Student's t-test showed that relative to the control group (cells treated with DMEM), p was less than 0.001 for both Krib and C8161 cells treated with sFN, as indicated by a star. The mean tumor weights in the other groups were not significantly different from that in the media control group. Shown is one of 3 experiments performed, in which similar results were obtained.

As shown in FIGS. 2A and 2B, mice that received Krib osteosarcoma (FIG. 2A) and C8161 melanoma (FIG. 2B) cells pre-incubated with sFN had significantly smaller tumors than the controls. About 30% of the animals that received sFN pre-treated tumor cells did not develop macroscopically detectable tumors even after 60 days. Recombinant fibronectin $III_1$-QE-C (SEQ ID NO:7) fragments alone and fibronectin alone had no effect on tumor implantation at the concentrations tested: 100 ug fibronectin per $10^6$ cells and 250 uM $III_1$-QE-C (SEQ ID NO:7) per $10^6$ cells.

sFN did not affect cell viability in these experiments, as demonstrated by MTT assay on aliquots of the cells prepared for injection into mice; cell viability was higher than 95% (results not shown). Trypan Blue exclusion also revealed greater than 95% viability in all treatment groups.

In conclusion, exposure of tumor cells to sFN inhibits their ability to form tumors in vivo. Specifically, the above experiments demonstrate that ex vivo sFN pretreatment of tumor cells inhibits the implantation and growth of subcutaneously inoculated C8161 melanoma and KRIB osteosarcoma cells.

EXAMPLE IV

Intravenously Circulating Tumor Cells Exposed to sFN are Inhibited from Metastasizing As demonstrated in this experimental metastasis study, the metastasis of intravenously circulating tumor cells can be inhibited by preexposure to sFN. Specifically, sFN pretreatment of Krib osteosarcoma and C8161 melanoma cells inhibited metastatic formation when these pretreated tumor cells were injected intravenously, as shown in FIG. 3.

In all experimental metastasis studies, $10^6$ cells in a 200 µl volume were injected into the tail vein of mice, 8 animals per group. In some experiments, the cells were treated with various forms of fibronectin. Experiments were terminated when a significant number of foci were detectable in the lungs of the control group mice. On the average this was about 3 to 6 weeks for experimental metastasis studies, which involve intravenous injection of tumor cells. For spontaneous metastasis studies, which involve inhibition of metastasis from pre-established tumors as in Example V, the experiments were terminated between 80 to 100 days. The extent of lung metastasis was assessed by: determining the number of macroscopic tumor foci identifiable under a dissecting microscope; lung weight; and, by histological examination of Hematoxylin/Eosin (H/E) stained lung sections. When macroscopically evident, the number of foci on the heart, thoracic wall, and axillary lymph nodes was also determined. The number of axillary lymph node metastatic foci from the C8161 melanoma was determined by visual inspection. Tumor masses were surgically removed, weighed, and fixed in Bouin's solution for histological analysis.

Tumor cells were pre-incubated for 10 minutes with sFN, media alone (DMEM), fibronectin, fibronectin with III-11-QE-C (SEQ ID NO:15) or $III_1$-QE-C (SEQ ID NO:7) alone. They were then injected into the tail vein at a concentration of $10^6$ cells/mouse, 6 mice per group. In FIG. 3A-1 the average lung weights in grams for DMEM, fibronectin, fibronectin with III-11-QE-C (SEQ ID NO:15), $III_1$-QE-C (SEQ ID NO:7) and sFN are 0.600, 0.585, 0.643, 0.460 and 0.230, respectively. In FIG. 3A-2 the average lung weights in grams for DMEM, fibronectin, fibronectin with III-11-QE-C (SEQ ID NO:15), $III_1$-QE-C (SEQ ID NO:7) and sFN are 0.590, 0.625, 0.708, 0.560 and 0.188, respectively. The standard error is shown for the KRIB osteosarcoma (FIG. 3A-1) and C8161 melanoma (FIG. 3A-2) experimental groups. Average normal lung weight (0.175 gram, ranging between 0.15 and 0.20) is indicated in the Figure and marked with a line. Relative to the media control group, p was less than 0.001 for both KRIB and C8161 cells treated with sFN, as indicated by a star. The other treatment groups were not significantly different from the DMEM group. FIG. 3A shows one of 5 experiments, in which similar results were obtained.

FIG. 3A gives the average weight in grams of lungs removed from animals. The experimental results demonstrate that the average weight of lungs removed from animals injected with sFN-treated Krib (FIG. 3A-1) or C8161 cells (FIG. 3A-2) were not significantly different from the weights of lungs taken from the animals not injected with tumor cells (see line which indicates average normal lung weight), whereas large metastatic loads were found in all the control groups (animals injected with cells treated with DMEM, fibronectin, fibronectin plus $III_1$-QE-C (SEQ ID NO:7) or III-1C alone). Histological exam confirmed that markedly decreased amounts of metastatic foci were present in mice injected with sFN-treated tumor cells (data not shown).

A similar effect of in vitro sFN pretreatment on the number of metastatic foci formed by intravenously injected C8161 cells on the thoracic wall (FIG. 3B-1) and on the heart (FIG. 3B-2) was seen. The average number of metastatic foci found on the thoracic wall for the DMEM, fibronectin, fibronectin with III-11-QE-C (SEQ ID NO:15), $III_1$-QE-C (SEQ ID NO:7) and sFN groups are 34.6, 49.8, 48.8, 30.6 and 3.0, respectively. The average number of metastatic foci found on the heart for the DMEM, fibronectin, fibronectin with III-11-QE-C (SEQ ID NO:15), $III_1$-QE-C (SEQ ID NO:7) and sFN groups are 11.8, 12.2, 12.8, 13.4 and 0.0, respectively. The number of C8161 melanoma metastatic foci found on the thoracic wall (FIG. 3B-1) and on the heart (FIG. 3B-2) is significantly decreased in mice injected with sFN-pretreated melanoma cells ($p<0.01$). One representative experiment out of 3 is shown. The sFN group differed significantly from the DMEM control group ($p<0.01$).

The HT-29 human colon carcinoma cell line was also tested in the intravenous injection assay. A similar effect of in vitro sFN pretreatment on the number of metastatic foci formed by intravenously injected HT-29 cells on the lungs (FIG. 3C-1) and in the lymph nodes (FIG. 3C-2) was seen. The average number of metastatic foci in the lungs removed from animals (FIG. 3C-1) for the DMEM, fibronectin, fibronectin with III-11-QE-C (SEQ ID NO:15), $III_1$-QE-C (SEQ ID NO:7) and sFN groups are 10.5, 11.0, 11.16, 10.5 and 1.16, respectively. The average weight of the metastatic foci in the lymph nodes removed from animals (FIG. 3C-2) for the DMEM, fibronectin, fibronectin with III-11-QE-C (SEQ ID NO:15), III$_1$-QE-C (SEQ ID NO:7) and sFN groups are 26.3, 28.8, 29.16, 23.16 and 0.0, respectively. The number of HT-29 lung metastatic foci (FIG. 3C-1) and average weight of the metastatic foci in the lymph nodes (FIG. 3C-2) were drastically reduced by sFN pre-treatment of the cells. As demonstrated in FIG. 3C, the number of lung metastatic foci and the weights of lymph node metastatic foci of mice injected intravenously with sFN pretreated HT-29 carcinoma cells was significantly less from the DMEM control group ($p<0.01$).

In conclusion, sFN inhibits the metastasis of intravenously circulating tumor cells exposed to sFN. Specifically, the above experiments show that ex vivo pre-treatment with sFN inhibits experimental metastasis of intravenously administered Krib osteosarcoma, C8161 melanoma and HT-29 carcinoma. Protected organs include the lungs, lymph nodes, heart and thoracic wall.

EXAMPLE V

Intraperitoneally Administered sFN Inhibits Metastasis from Established Solid Tumors Intraperitoneally injected sFN causes a specific and significant decrease in the number of metastatic foci resulting from tumor cells in circulation. Intraperitoneally administered sFN also inhibits spontaneous metastasis from pre-established tumors.

Intraperitoneally injected sFN caused a specific and significant decrease in the number of lung metastatic foci resulting from tumor cells injected intravenously. FIG. 4A demonstrates this with both the Krib osteosarcoma (FIG. 4A-1) and the C8161 melanoma cells (FIG. 4A-2). The cells were injected intravenously, $10^6$ cells per mouse, 6 mice per group. The animals were injected intraperitoneally with the various agents 30 minutes prior to injection of the tumor cells into the tail vein, and 30 minutes and 4 hours after it. Media alone (DMEM), fibronectin, fibronectin with III-11-QE-C (SEQ ID NO:15), III$_1$-QE-C (SEQ ID NO:7) alone or sFN were injected into the peritoneal cavity.

For producing sFN for intraperitoneal administration, fibronectin can be mixed with recombinant fragments at a molar ratio of about 1:50, where 100 µg of fibronectin is incubated with 30 µl of III$_1$-QE-C (SEQ ID NO:7) at 500 µM, as described in Example II.

Individual control-treated mice were sacrificed at different time intervals and the entire experiment terminated when metastatic foci were observed in a random sample of control-treated mice. The average number of KRIB metastatic foci on the lungs in mice treated with DMEM, fibronectin, fibronectin with III-11-QE-C (SEQ ID NO:15), III$_1$-QE-C (SEQ ID NO:7) and sFN was 59.6, 63.1, 57.6, 58.1 and 28.3, respectively (FIG. 4A-1). The average number of C8161 metastatic foci on the lungs of mice treated with DMEM, fibronectin, fibronectin with III-11-QE-C (SEQ ID NO:15), III$_1$-QE-C (SEQ ID NO:7) and sFN was 22.5, 17.8, 16.8, 22.6 and 12.5, respectively (FIG. 4A-2). As FIG. 4A demonstrates, the sFN-treated mice showed significantly less metastatic growth in the lungs than the controls.

FIGS. 4B and 4C demonstrate the inhibitory effect of intraperitoneally administered sFN on spontaneous metastasis from pre-established subcutaneous tumors. Mice were inoculated with untreated Krib osteosarcoma and C8161 melanoma tumor cells subcutaneously. The tumors were allowed to grow to about 6 mm in diameter (approximately 15 days), and the mice were then treated with intraperitoneal sFN or control injections, as shown in FIGS. 4B and 4C. Individual control-treated mice were sacrificed at different time intervals and the entire experiment terminated when metastatic foci were observed in a random sample of control-treated mice.

FIGS. 4B-1 and 4C-1 show the average weight of the primary subcutaneous tumor in grams, and FIGS. 4B-2 and 4C-2 show the average number of metastatic foci on the lungs. The average weight in grams of the KRIB primary tumors in mice treated with DMEM, fibronectin, fibronectin with III-11-QE-C (SEQ ID NO:15), III$_1$-QE-C (SEQ ID NO:7) and sFN was 35.4, 38.0, 33.6, 33.3 and 33.66, respectively (FIG. 4B-1). The average number of KRIB metastatic foci on the lungs in the mice treated with DMEM, fibronectin, fibronectin with III-11-QE-C (SEQ ID NO:15), III$_1$-QE-C (SEQ ID NO:7) and sFN was 21.8, 20.3, 22.16, 18.3 and 6.1, respectively (FIG. 4B-2). The average weight in grams of the C8161 primary tumors in mice treated with DMEM, fibronectin, fibronectin with III-11-QE-C (SEQ ID NO:15), III$_1$-QE-C (SEQ ID NO:7) and sFN was 6.47, 6.5, 3.4, 6.72 and 6.0, respectively (FIG. 4C-1). The average number of C8161 metastatic foci on the lungs in mice treated with DMEM, fibronectin, fibronectin with III-11-QE-C (SEQ ID NO:15), III$_1$-QE-C (SEQ ID NO:7) and sFN was 16.75, 18.5, 19.0, 17.5 and 9.75, respectively (FIG. 4C-2). These experiments demonstrate that the sFN-treated mice showed significantly less metastatic growth than the controls, while the size of primary tumors was not affected.

Figure 4D:
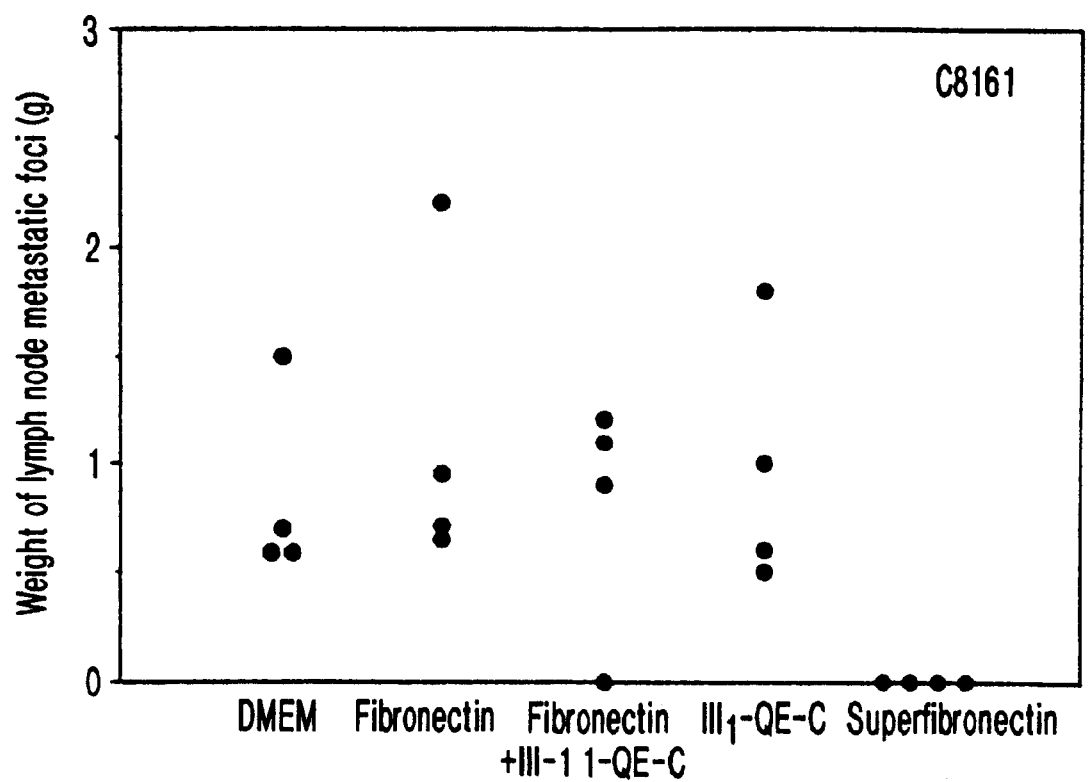

FIG. 4D demonstrates that sFN prevented formation of lymph node metastases from pre-established subcutaneous C8161 melanoma tumors. The average weight in grams of the lymph node metastastic foci for mice treated with DMEM, fibronectin, fibronectin with III-11-QE-C (SEQ ID NO:15), III$_1$-QE-C (SEQ ID NO:7) and sFN was 0.85, 1.11, 0.8, 1.01 and 0.0, respectively. In control-treated mice, the C8161 sub-cutaneous melanoma tumors produced predominantly lymph node metastases. No detectable metastatic C8161 foci were found in the lungs, even four months after the inoculation. Lymph node metastases were found only in control-treated mice. As the data in FIG. 4D demonstrates, the mice treated intraperitoneally with sFN had no evidence of lymph node melanoma cell metastasis.

For all spontaneous metastasis studies, $10^6$ cells were implanted subcutaneously on the left flank of the mice (4-5 mice per group). When the tumors reached 6 mm in diameter, various treatments were administered intraperitoneally every 3 days, and the animals were monitored daily. At several time points from the $30^{th}$ day on, single animals from the control groups were sacrificed, the number of metastatic foci in their lungs was determined under a dissecting microscope, and a histological examination was performed after fixation of the tissue. Additional animals were inoculated in the control groups for this purpose.

Systemic absorption of $^{125}$I-labeled sFN after intraperitoneal administration was monitored as follows: 100 µg of fibronectin were labeled using Iodogen (Sigma, St. Louis, Mo.), as described in Morla, A., et al., (1994) supra, and the labeled fibronectin was incubated with III$_1$-QE-C (SEQ ID NO:7) as described above, and the mixture was injected intraperitoneally. Tail vein bleeds were done at the indicated times and blood was analyzed under non-reducing conditions by SDS-PAGE followed by autoradiography.

In conclusion, intraperitoneally injected sFN causes a specific and significant decrease in the number of lung metastatic foci resulting from circulating tumor cells. Specifically, this was demonstrated with both the osteosarcoma and the melanoma tumor cells. It was also demonstrated that intraperitoneally administered sFN inhibits spontaneous metastasis from pre-established subcutaneous tumors. Specifically, lung and lymph node metastases from osteosarcoma and melanoma primary tumors, respectively, are inhibited by the systemic administration of sFN.

EXAMPLE VI

Superfibronectin is Effective in Reducing the Spread of Tumors within the Peritoneal Cavity To demonstrate that sFN is effective in reducing the spread of tumors within the peritoneal cavity, a series of experiments was carried out with an ovarian cancer model. As demonstrated in FIG. 5, data indicates that sFN is effective in reducing the spread of ovarian tumors within the peritoneal cavity.

As described in Example III, female nude mice, 2 months old (Harlan Sprague Dawley, San Diego, Calif.) were used in all studies. The OVCAR-3 ovarian carcinoma cells were cultured as described in Hamilton et al., (1983), and were not in continuous culture for more than three consecutive passages prior to the experiments. Culture medium was changed 12 hours before cells were injected into mice. Cells were detached with PBS containing 2.5 mM EDTA from monolayers that had reached 80% confluence, washed three times with DMEM, counted, and resuspended in DMEM. Cell viability was monitored by Trypan Blue exclusion.

The harvested cells, $10^8$ per animal, in 200 ul of DMEM, were injected into the peritoneal cavity. Fifteen minutes after the injection, animals were divided in two groups and treated intraperitoneally with sFN. The sFN is generated by mixing 100 ug of fibronectin with the $III_1$-QE-C (SEQ ID NO:7) fragment at a molar ratio of 1:150, as described above, or media (DMEM) only. The experiment was terminated after 80 days, and the number of tumor foci on the intestines, peritoneal wall and the ovaries was determined under a dissection microscope. The number of foci on the ovaries was confirmed by histological examination of Hematoxylin/Eosin-stained (H/E) sections.

Figure 5A:
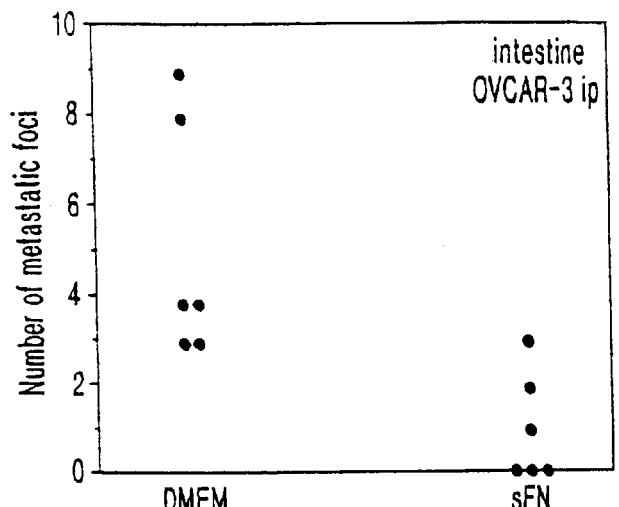
FIGS. 5A, 5B and 5C demonstrate that sFN is effective in reducing the spread of tumors within the peritoneal cavity.
Figure 5B:
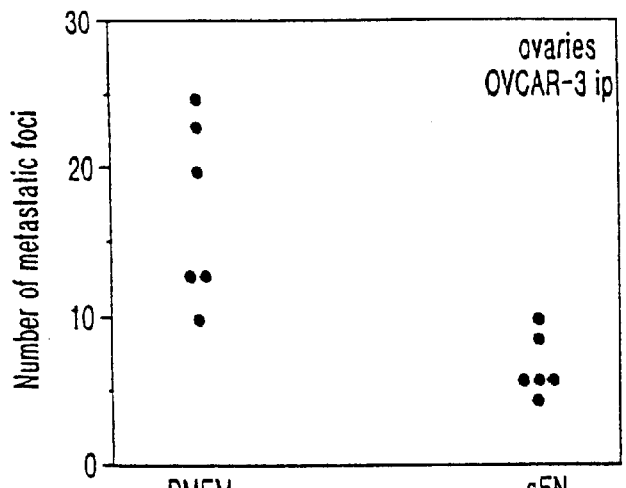
Figure 5C:
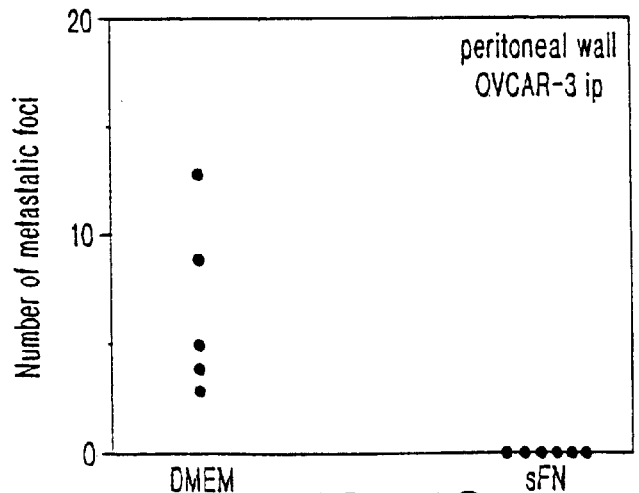

FIG. 5 demonstrates the effect of sFN on the spreading of the intraperitoneally injected human ovarian carcinoma cells. The average number of tumor foci on the intestinal lining (FIG. 5A) after DMEM and sFN treatment was 5.1, 1.0., respectively. The average number of tumor foci in the ovaries (FIG. 5B) after DMEM and sFN treatment was 16.6, 6.3, respectively. The average number of tumor foci on the peritoneal wall (FIG. 5C) after DMEM and sFN treatment was 6.0, 0.0, respectively. The number of metastatic foci in animals treated with sFN was significantly fewer than in the control animals.

In conclusion, intraperitoneally injected sFN causes a specific and significant decrease in the number of intraperitoneal metastatic foci resulting from tumor cells injected intraperitoneally. Specifically, this was demonstrated by the injection of OVCAR-3 ovarian cancer cells followed by sFN administration, which inhibited metastatic foci formation on the peritoneal wall and etastatic foci associated the intestines and associated with the ovaries.

EXAMPLE VII

Superfibronectin and sFN-Generating Fragments Cause Regression of Established Primary Tumor In Vivo To demonstrate that sFN and sFN-inducing fragments are effective in causing the regression of established primary tumors in vivo, a series of experiments was carried out with osteosarcoma, hemangioma and breast carcinoma tumors in which treatments were injected into the tumor area.

Figure 6A:
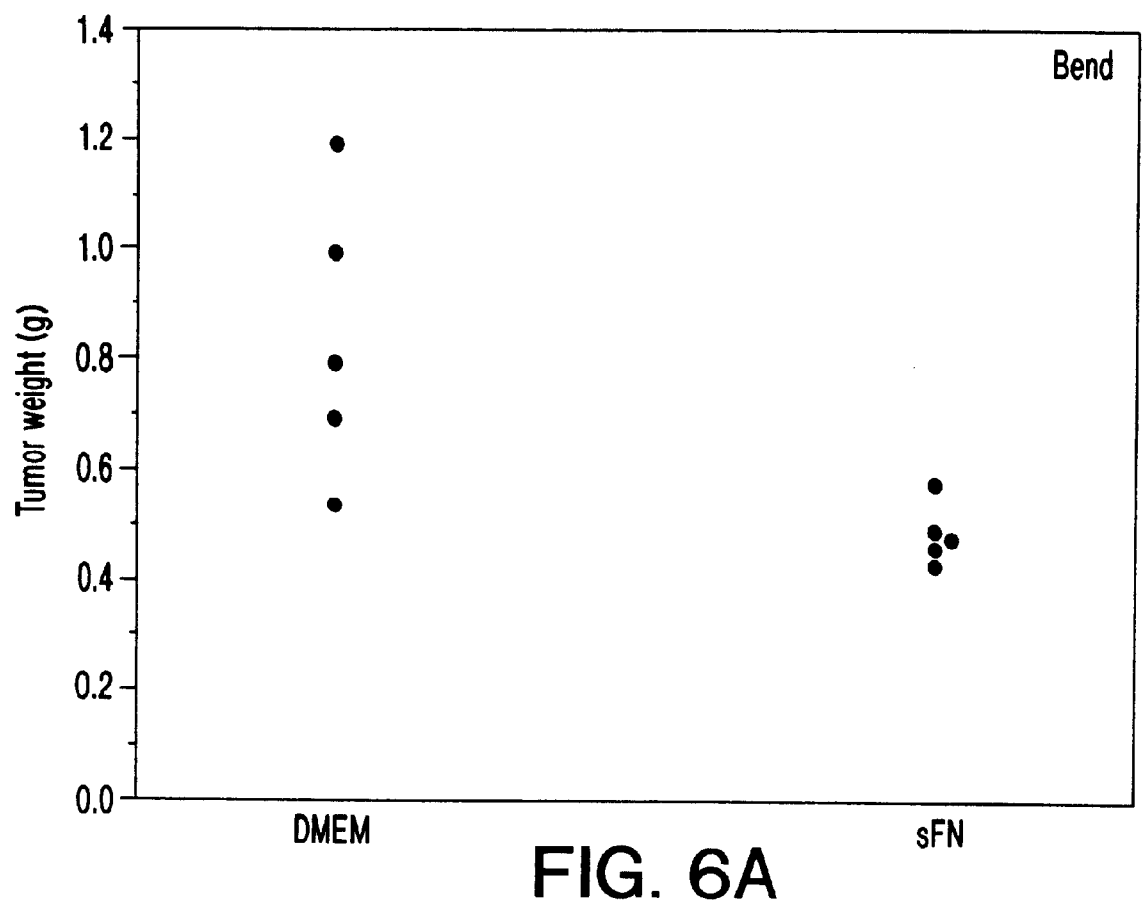
FIGS. 6A, 6B, 6C, 6D and 6E demonstrate that sFN is able to suppress the growth of primary tumor and cause it to regress. Specifically.
Figure 6B:
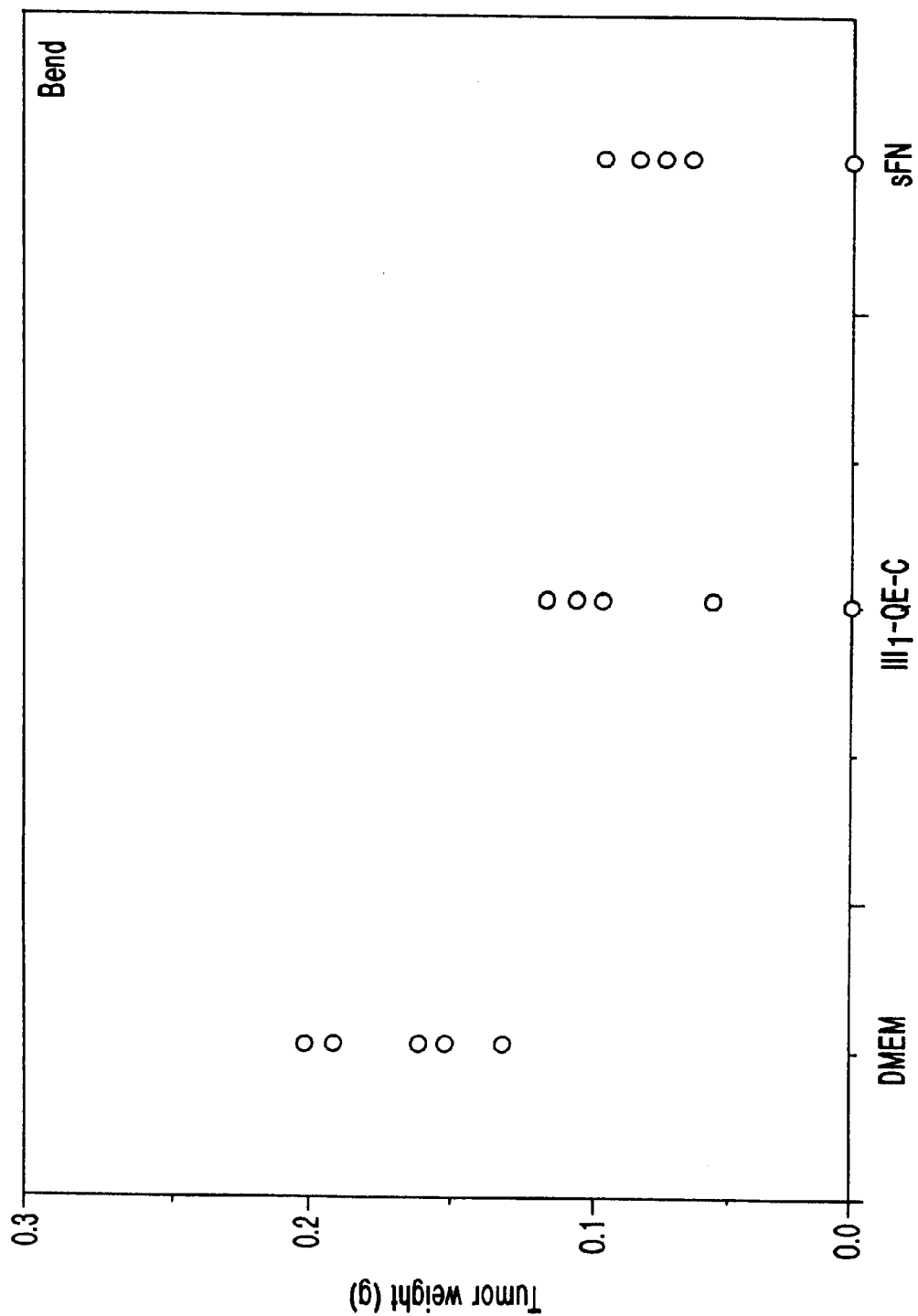
Figure 6C:
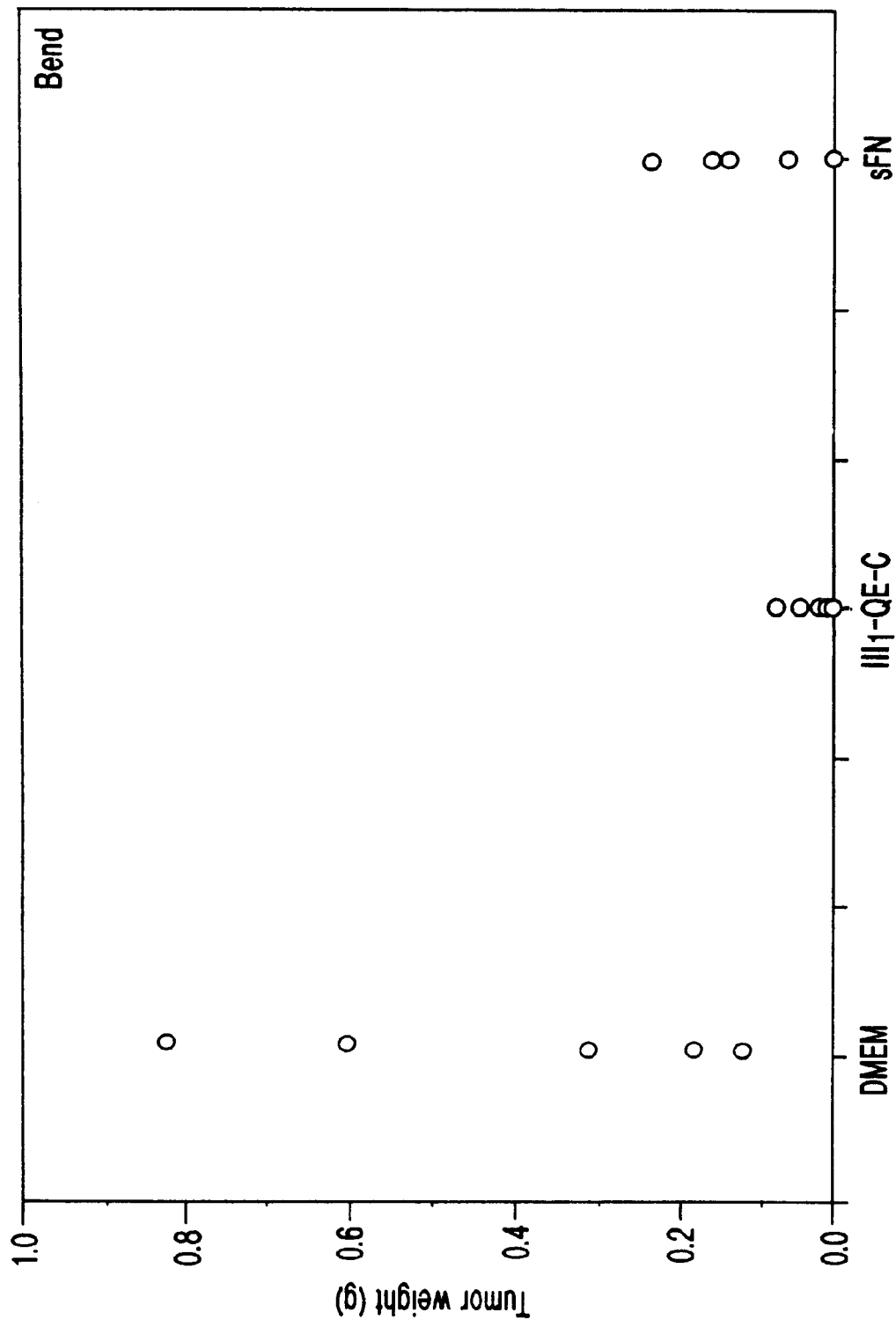
Figure 6D:
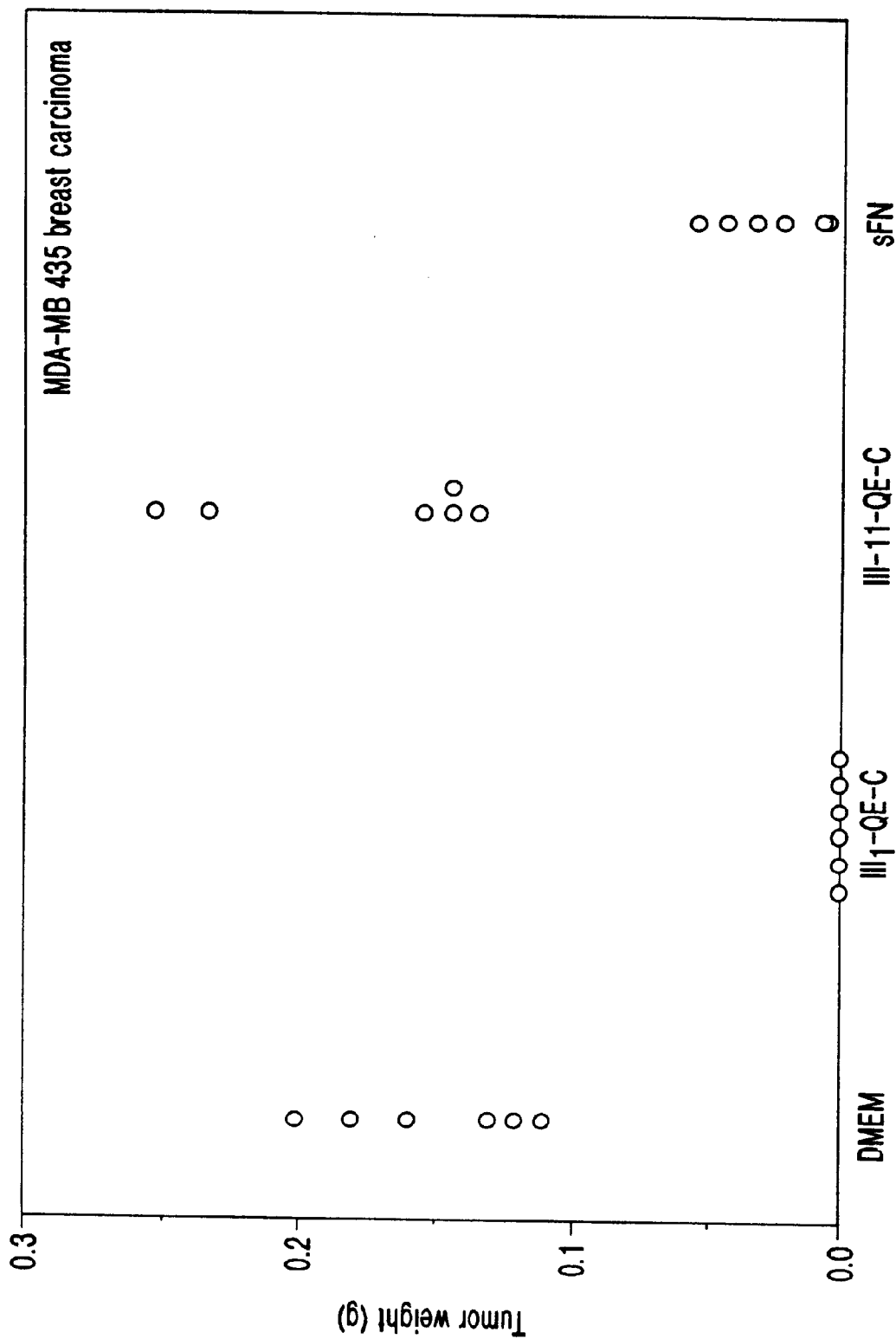

As demonstrated in FIGS. 6A and 6B, data indicates that sFN and the sFN-generating recombinant peptide $III_1$-QE-C (SEQ ID NO:7) cause regression of endothelial cell tumors upon injection peritumorally. FIG. 6D demonstrates that sFN is effective in causing the regression of established breast carcinoma tumors.

The hemangioma (endothelial) Bend tumor cell line was maintained as described in Montesano, R., et al., Cell 62:435–445 (1990), and prepared for the experiments as described above for the OVCAR ovarian tumor cells in Example VI. For FIG. 6A, $10^8$ cells per animal were inoculated subcutaneously on the left flank of mice. After 7 days, animals bearing tumors of approximately 6 mm in diameter were selected and divided into 2 groups (5 to 6 animals per group). The first group was treated with 200 ul of media only (DMEM), which was injected into several sites about 2 mm from the tumor. The second group received sFN, prepared as in Example VI, and injected peritumorally the same as the controls. These treatments were given weekly for three weeks. The animals were then sacrificed and the macroscopic tumors removed and weighed.

FIG. 6A shows tumor weights from one of three experiments that produced similar results. The average tumor weight in grams after DMEM and sFN administration was 0.84 and 0.50, respectively. The tumors in the sFN group are significantly smaller than in the control group, with the p value for sFN versus the control group less than 0.02. Histological analysis (Bouin's fixation, H/E sections) revealed substantial thinning of the cell layer lining blood filled cavities in the sFN group relative to the control group.

The responsiveness of established primary C8161 melanoma and KRIB osteosarcoma cell tumors to peritumorally injected sFN was also evaluated. No effect on these tumors was seen.

The sFN-generating recombinant peptide $III_1$-QE-C (SEQ ID NO:7) was also demonstrated to cause regression of Bend cell hemangiomas upon injection peritumorally. Bend tumor cells were innoculated subcutaneously into the left flank of mice, $10^6$ cells per animal. When the tumors reached approximately 1 cm in diameter, the mice were divided into three groups. The first group was treated with 200 ul of media (DMEM) only. The second group was injected with sFN, prepared as described above. The third group was injected with 200 $\mu$l of a 500 $\mu$M $III_1$-QE-C (SEQ ID NO:7) fragment solution. All injections were into three sites about two millimeters from the tumor. The treatments were given weekly for three weeks. The animals were then sacrificed and the macroscopic tumors removed and weighed. FIG. 6B shows the tumor weights in grams. The average tumor weight in grams of the DMEM, the $III_1$-QE-C (SEQ ID NO:7) fragment solution and sFN are 0.128, 0.082 and 0.058, respectively. The p value for sFN and $III_1$-QE-C (SEQ ID NO:7) versus the control group is less than 0.001. These data demonstrate that both the sFN and the $III_1$-QE-C (SEQ ID NO:7) treated groups had significantly fewer subcutaneous tumors than the control, media only, treated group.

Ex vivo pretreatment of tumor cells with sFN or the sFN-generating recombinant peptide $III_1$-QE-C (SEQ ID NO:7) reflected the results from the peritumoral injection experiments. Hemangioma (endothelial) Bend tumor cells were injected subcutaneously after pretreatment with either media only, sFN or $III_1$-QE-C (SEQ ID NO:7). $III_1$-QE-C (SEQ ID NO:7) solution was at 250 μM and the sFN was prepared by mixing 100 μg of fibronectin with 100 μl of 500 μM III$_1$-QE-C (SEQ ID NO:7). The pretreated Bend tumor cells were then innoculated sub-cutaneously into the left flank of the mice, $10^6$ cells per animal. After three weeks the animals were sacrificed and the macroscopic tumors removed and weighed. FIG. 6C shows the tumor weights in grams. The average tumor weight in grams of the DMEM, the III$_1$-QE-C (SEQ ID NO:7) fragment solution and sFN are 0.41, 0.186 and 0.098, respectively. The p value for sFN and III$_1$-QE-C (SEQ ID NO:7) versus the control group is less than 0.001. These data demonstrate that the sFN and the III$_1$-QE-C (SEQ ID NO:7) treated groups had significantly fewer subcutaneous tumors than the control, media only, treated group.

Established breast carcinoma tumors were also responsive to local in vivo treatment with sFN. Human breast carcinoma cells used were derived from the cell line MDA-MB-435, as described in Price, J. E., et al., *Cancer Res.* 50:717–721 (1990). Their responsiveness to sFN was first established in an ex vivo treatment experiment. FIG. 6D shows that ex vivo treatment of MDA-MB-435 breast carcinoma cells with sFN and the sFN-generating recombinant peptide III$_1$-QE-C (SEQ ID NO:7) inhibited tumor formation in vivo. To demonstrate this effect, MDA-MB-435 cells were inoculated into the mammary fat pad after ex vivo pretreatment with either media only, sFN or III$_1$-QE-C (SEQ ID NO:7). The III$_1$-QE-C (SEQ ID NO:7) solution was at 250 μM and the sFN was prepared by mixing 100 μgm of fibronectin with 100 μl of 500 μM III$_1$-QE-C (SEQ ID NO:7), as described above. The pretreated tumor cells were then innoculated into the mammary fat pads of the mice, $10^6$ cells per animal. After three weeks the animals were sacrificed and the macroscopic tumors removed and weighed. FIG. 6D shows the tumor weights in grams. The average weight in grams of the tumors removed from mice treated with DMEM, III$_1$-QE-C (SEQ ID NO:7), III-11-QE-C (SEQ ID NO:15) and sFN is 0.145, 0.0, 0.18, 0.029, respectively, and the p values are 0.0, 0.2 and 0.0, respectively, in comparison to DMEM. These data demonstrate that both the sFN and the III$_1$-QE-C (SEQ ID NO:7) treated groups had significantly smaller subcutaneous breast carcinoma tumors than the control, media only-treated, group.

Figure 6E:
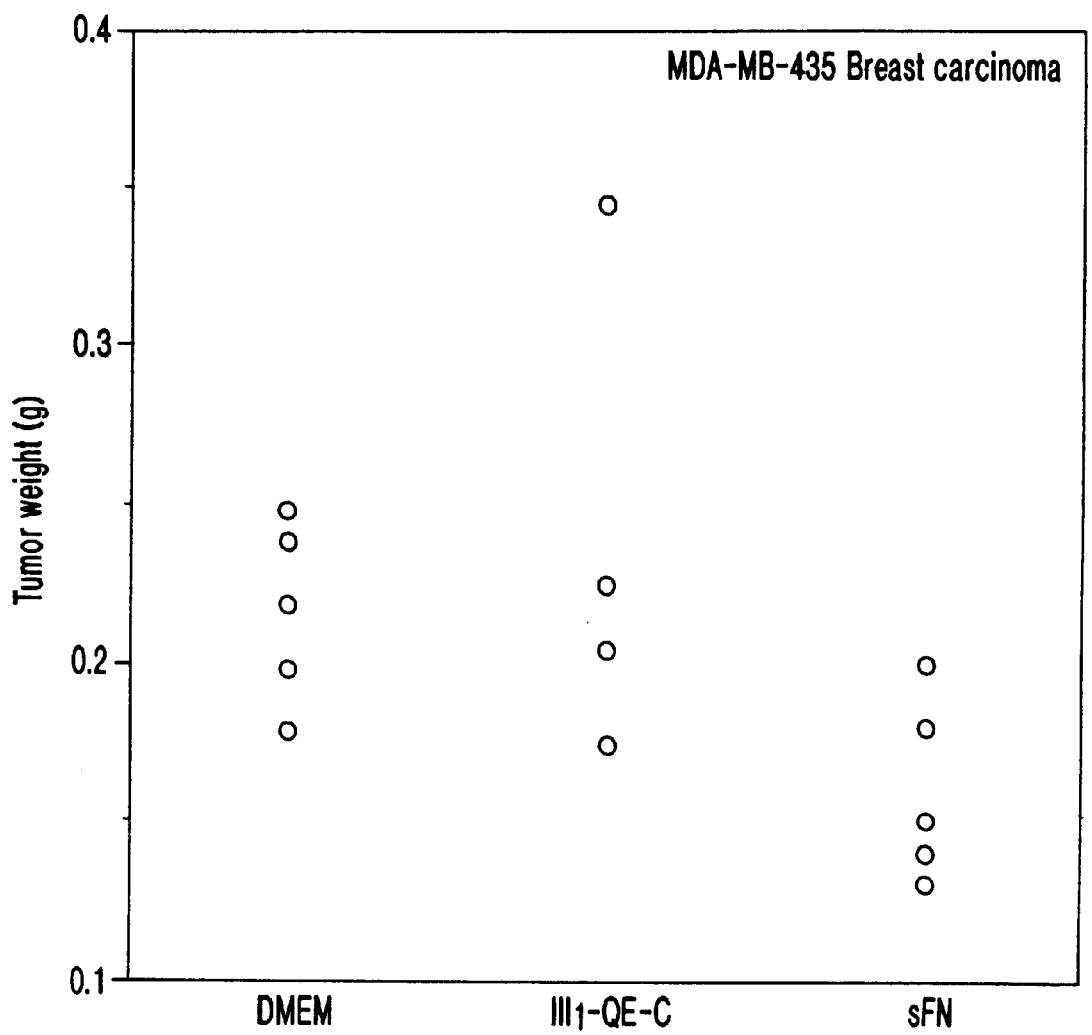

To study the effect of local sFN treatment on MDA-MB-435 tumors in vivo, the same experiment as described for FIG. 6A was done except: that MDA-MB-435 cells were innoculated; and, the tumors were allowed to reach up to approximately 0.2 inches in diameter. FIG. 6E shows the tumor size in inches. The average weight in grams of the tumors removed from mice treated with DMEM, III$_1$-QE-C (SEQ ID NO:7) and sFN is 0.21, 0.23, 0.17, respectively. The p values are 0.56 and 0.05 for III$_1$-QE-C (SEQ ID NO:7) and sFN compared to DMEM, respectively. As demonstrated by this data, the sFN treated group had significantly smaller subcutaneous tumors than the III$_1$-QE-C (SEQ ID NO:7) and the control, media only, treated group.

In conclusion, these results demonstrate that the antitumor effects of sFN and sFN-generating compounds are not limited to inhibition of metastasis or tumor growth, but also include their ability to cause regression of established primary tumors. Specifically, these data demonstrate that peritumorally administered sFN or sFN-generating fragment III$_1$-QE-C (SEQ ID NO:7) can cause the regression of established primary hemangioma cell (endothelially-derived) tumors in vivo. Furthermore, peritumorally administered sFN and sFN-generating compound can cause the regression of established breast carcinoma tumors.

EXAMPLE VIII sFN Interferes with Cell Spreading and Migration

Figures 1, 7A:
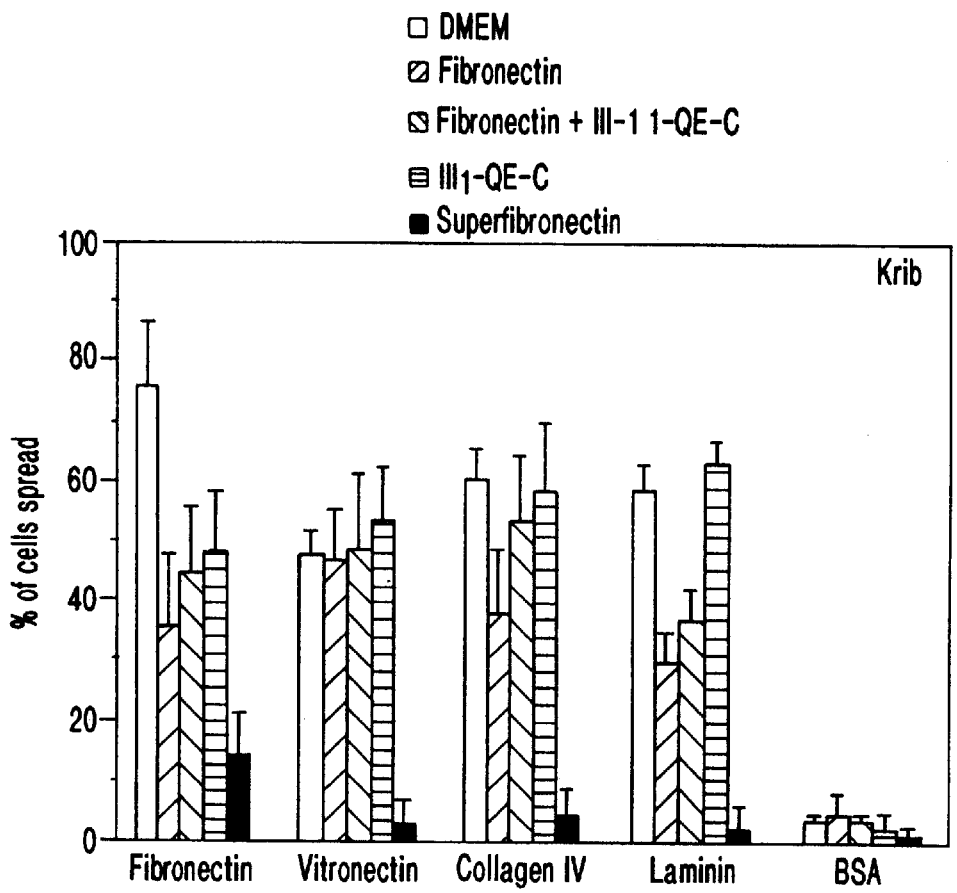
Figures 2, 7A:
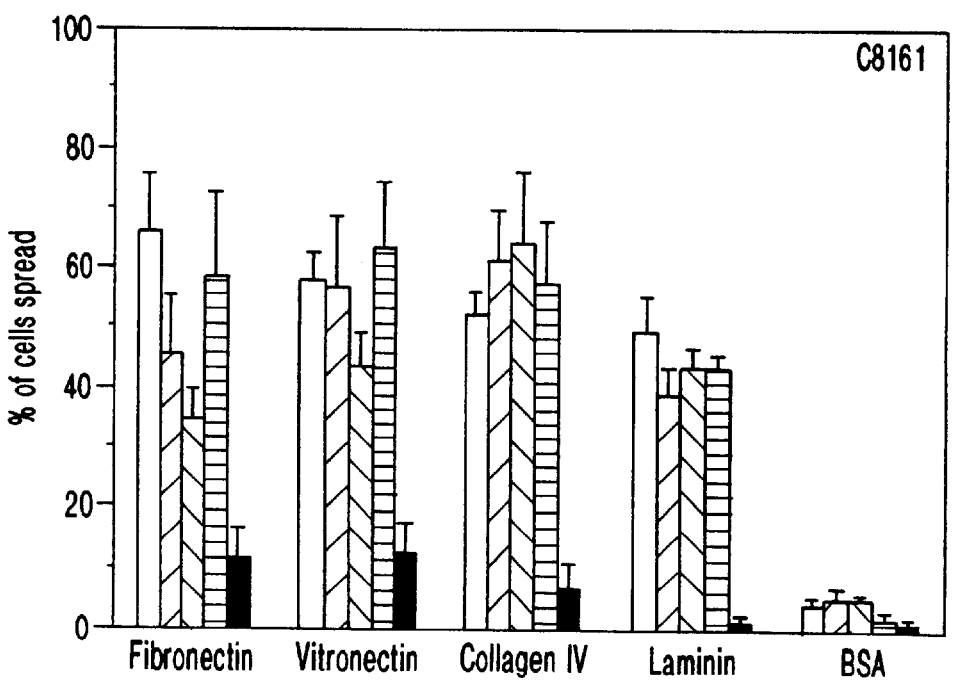
Figures 1, 7B:
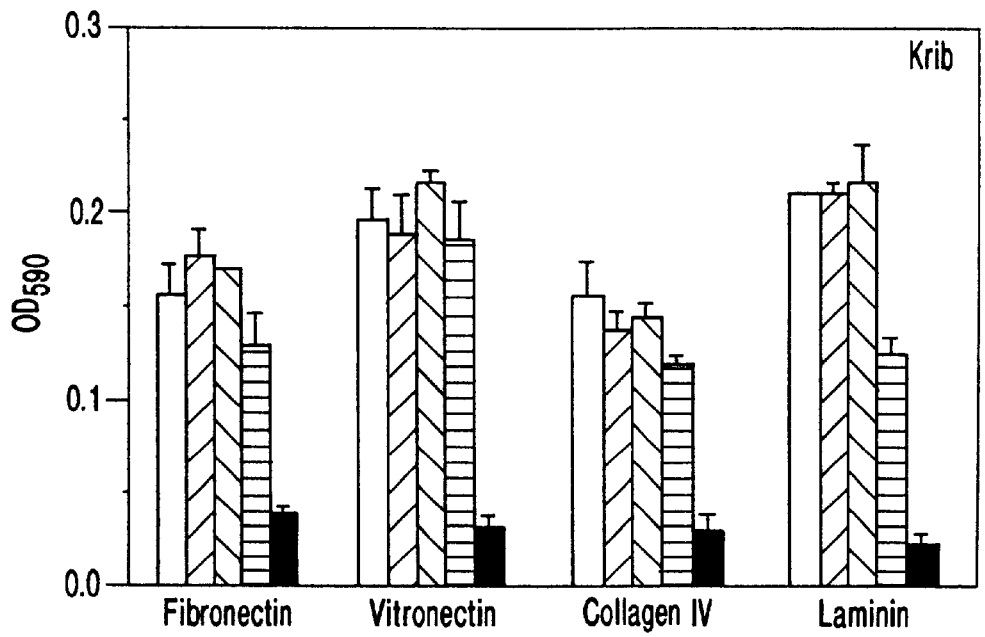
Figures 2, 7B:
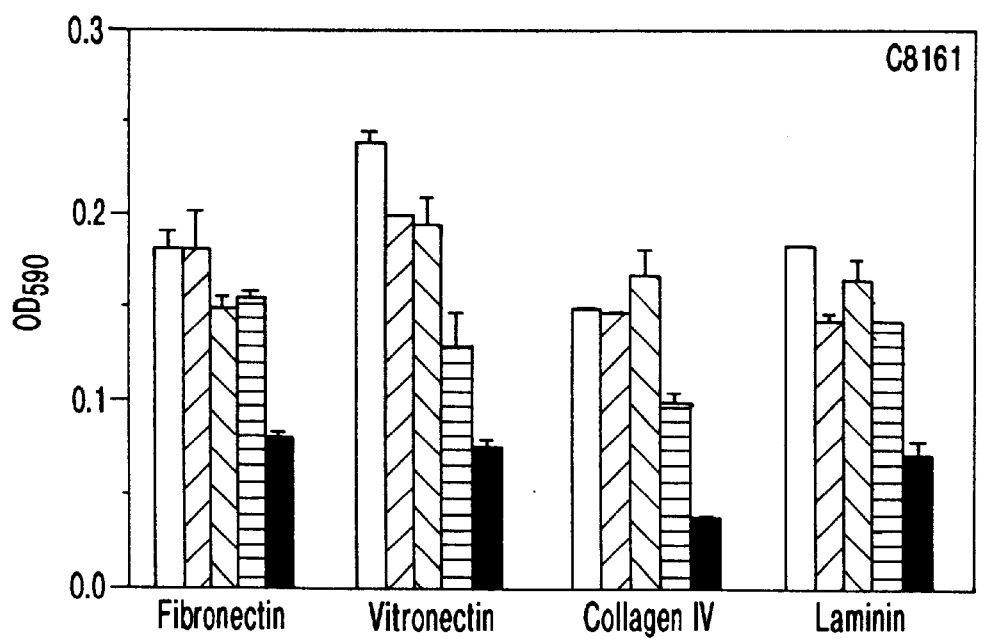

To demonstrate mechanisms responsible for sFN's inhibitory effect on metastasis, the effect of sFN on cell spreading and migration in vitro was studied, as described in FIGS. 7A and 7B, respectively.

FIG. 7A shows results from a cell spreading assay. KRIB osteosarcoma (FIG. 7A-1) and C8161 melanoma (FIG. 7A-2) cell spreading was assessed on 48-well plates (Costar, Cambridge, Mass.), which were coated with 10 μg/ml of fibronectin, laminin (Gibco BRL, Bethesda, Md.), collagen IV (Collaborative Research, Bedford, Mass.), vitronectin (Gibco BRL, Bethesda, Md.) or bovine serum albumin (BSA, a negative control) in PBS, overnight at 4° C. Cells were pre-treated with sFN, prepared as described above, at 1:150 fibronectin to III-1C ratio, or control materials (DMEM, fibronectin alone, fibronectin and III$_1$-QE-C (SEQ ID NO:7), and III-1C alone); incubated for 10 minutes at room temperature; plated at $5\times10^4$ cell per well; and, allowed to spread for 3 hours at 37° C., 5% $CO_2$, on the pre-coated membranes. After 4 h, the percentage of input cells that had spread (any cell that is not "round" is counted as "spread") was determined by scoring at least 3 microscopic fields in triplicate wells.

As demonstrated in FIG. 7A-1, the percentage of Krib osteosarcoma cells that had spread in fibronectin-precoated wells after treatment with DMEM, fibronectin, III-11-QE-C (SEQ ID NO:15), III$_1$-QE-C (SEQ ID NO:7) and sFN was 76%, 36%, 45%, 49% and 15%, respectively. The percentage of Krib cells that had spread in vitronectin-precoated wells after treatment with DMEM, fibronectin, III-11-QE-C (SEQ ID NO:15), III$_1$-QE-C (SEQ ID NO:7) and sFN was 49%, 48%, 50%, 55% and 4%, respectively. The percentage of Krib cells that had spread in collagen IV-precoated wells after treatment with DMEM, fibronectin, III-11-QE-C (SEQ ID NO:15), III$_1$-QE-C (SEQ ID NO:7) and sFN was 62%, 40%, 55%, 60% and 5%, respectively. The percentage of Krib cells that had spread in laminin-precoated wells after treatment with DMEM, fibronectin, III-11-QE-C (SEQ ID NO:15), III$_1$-QE-C (SEQ ID NO:7) and sFN was 60%, 33%, 38%, 65% and 2%, respectively. The percentage of Krib cells that had spread in BSA-precoated wells after treatment with DMEM, fibronectin, III-11-QE-C (SEQ ID NO:15), III$_1$-QE-C (SEQ ID NO:7) and sFN was 3%, 4%, 3%, 2% and 1%, respectively.

As demonstrated in FIG. 7A-2, the percentage of C8161 melanoma cells that had spread in fibronectin-precoated wells after treatment with DMEM, fibronectin, III-11-QE-C (SEQ ID NO:15), III$_1$-QE-C (SEQ ID NO:7) and sFN was 66%, 46%, 35%, 59% and 12%, respectively. The percentage of C8161 cells that had spread in vitronectin-precoated wells after treatment with DMEM, fibronectin, III-11-QE-C (SEQ ID NO:15), III$_1$-QE-C (SEQ ID NO:7) and sFN was 59%, 58%, 45%, 65% and 14%, respectively. The percentage of C8161 cells that had spread in collagen IV-precoated wells after treatment with DMEM, fibronectin, III-11-QE-C (SEQ ID NO:15), III$_1$-QE-C (SEQ ID NO:7) and sFN was 52%, 62%, 65%, 58% and 8%, respectively. The percentage of C8161 cells that had spread in laminin-precoated wells after treatment with DMEM, fibronectin, III-11-QE-C (SEQ ID NO:15), III$_1$-QE-C (SEQ ID NO:7) and sFN was 50%, 51%, 45%, 45% and 1%, respectively. The percentage of C8161 cells that had spread in BSA-precoated wells after treatment with DMEM, fibronectin, III-11-QE-C (SEQ ID NO:15), III$_1$-QE-C (SEQ ID NO:7) and sFN was 4%, 5%, 5%, 2% and 1%, respectively.

Untreated KRIB osteosarcoma and C8161 melanoma cells (FIGS. 7A-1 and 7A-2, respectively) and HT-29 cells (not shown), pretreated with fibronectin, fibronectin and III-11-QE-C (SEQ ID NO:15), III$_1$-QE-C (SEQ ID NO:7) and DMEM, attached to, i.e. spread onto, the immobilized human extracellular matrix proteins fibronectin, vitronectin, collagen IV and laminin. This was in agreement with the expression of a number of integrins, including several fibronectin receptors at the surface of these cells, as described in Table 1. However, after preincubation with sFN, both KRIB and C8161 cells were unable to spread on any of the immobilized human extracellular matrix proteins or on BSA. The difference between sFN and control treatments was clear at all time points assessed and was seen even 24 hours after the plating.

FIG. 7B shows optical density (OD$_{590}$) readouts from a cell migration assay using fibronectin, laminin, collagen IV, and vitronectin substrates coating Boyden chamber membranes. KRIB osteosarcoma (FIG. 7B-1) cells and C8161 melanoma cells (FIG. 7B-2) were pre-treated with sFN or control materials (DMEM, fibronectin alone, fibronectin and III$_1$-QE-C (SEQ ID NO:7), and III$_1$-QE-C alone) and allowed to migrate for 3 h in Boyden chambers containing the pre-coated membranes. The number of cells that migrated was assessed by dying the membranes of cells that had migrated and then measuring the optical density (absorbance at 590 nm) of the eluted dye (details described below). The results of this quantitative analysis for each group in FIG. 7B are listed below. The greater the number of migratory cells, the higher the optical density (OD$_{590}$) readout number.

As demonstrated in FIG. 7B-1, the optical density (OD$_{590}$) readout for KRIB osteosarcoma cells migrating through fibronectin-precoated membranes after treatment with DMEM, fibronectin alone, fibronectin and III$_1$-QE-C (SEQ ID NO:7), III$_1$-QE-C alone and sFN was 0.157, 0.177, 0.17, 0.129 and 0.038, respectively. The optical density (OD$_{590}$) readout for KRIB cells migrating through vitronectin-precoated membranes after treatment with DMEM, fibronectin alone, fibronectin and III$_1$-QE-C (SEQ ID NO:7), III$_1$-QE-C alone and sFN was 0.197, 0.19, 0.217, 0.187 and 0.032, respectively. The optical density (OD$_{590}$) readout for KRIB cells migrating through collagen IV-precoated membranes after treatment with DMEM, fibronectin alone, fibronectin and III$_1$-QE-C (SEQ ID NO:7), III$_1$-QE-C alone and sFN was 0.157, 0.139, 0.145, 0.121 and 0.031, respectively. The optical density (OD$_{590}$) readout for KRIB cells migrating through laminin-precoated membranes after treatment with DMEM, fibronectin alone, fibronectin and III$_1$-QE-C (SEQ ID NO:7), III$_1$-QE-C alone and sFN was 0.210, 0.211, 0.216, 0.126 and 0.023, respectively.

As demonstrated in FIG. 7B-2, the optical density (OD$_{590}$) readout for C8161 melanoma cells migrating through fibronectin-precoated membranes after treatment with DMEM, fibronectin alone, fibronectin and III$_1$-QE-C (SEQ ID NO:7), III$_1$-QE-C alone and sFN was 0.183, 0.183, 0.150, 0.156 and 0.082, respectively. The optical density (OD$_{590}$) readout for C8161 cells migrating through vitronectin-precoated membranes after treatment with DMEM, fibronectin alone, fibronectin and III$_1$-QE-C (SEQ ID NO:7), III$_1$-QE-C alone and sFN was 0.241, 0.203, 0.198, 0.133 and 0.078, respectively. The optical density (OD$_{590}$) readout for C8161 cells migrating through collagen IV-precoated membranes after treatment with DMEM, fibronectin alone, fibronectin and III$_1$-QE-C (SEQ ID NO:7), III$_1$-QE-C alone and sFN was 0.153, 0.151, 0.171, 0.104 and 0.042, respectively. The optical density (OD$_{590}$) readout for C8161 cells migrating through laminin-precoated membranes after treatment with DMEM, fibronectin alone, fibronectin and III$_1$-QE-C (SEQ ID NO:7), III$_1$-QE-C alone and sFN was 0.188, 0.148, 0.168, 0.147 and 0.075, respectively.

As demonstrated by the cell migration assay in FIG. 7B, sFN inhibited the migration of the Krib osteosarcoma (FIG. 7B-1) and C8161 melanoma cells (FIG. 7B-2) on fibronectin, vitronectin, type IV collagen, and laminin-coated wells by about 70%.

To provide a basis for the in vitro studies of FIG. 7, the integrin surface expression profile on the tumor cell lines was determined by flow cytometric analysis as described in Pasqualini, R., et al., *J. Cell. Biol.* 125:447–460 (1994). Monoclonal antibodies against the human $\alpha_2$ (AK-7), and $\alpha_4$ (9F10) subunits were from Pharmingen (La Jolla, Calif.), anti-$\beta_3$ (CD-61) was from Becton and Dickinson (San Jose, Calif.), anti-$\beta_4$ (3E1) was from Gibco BRL (Bethesda, Md.), anti-$\alpha_5$ from Oncogene Science (Cambridge, Mass.), anti-$\alpha_v$ from Chemicon (Temecula, Calif.), anti-$\beta_1$ (TS2/16), anti-$\beta_5$ (IA9), anti-$\alpha_1$ (TS2/7), anti-$\alpha_6$ (BQ16), and anti-$\alpha_3$ (IVA5) were a gift from Dr. Martin Hemler (Dana Farber Cancer Institute, Harvard Medical School); the anti-$\beta_8$ (SN-1) was from Dr. Robert Pytela (University of California, San Francisco), anti-$\beta_6$ (9G6) and anti $\alpha_9$ (Y9A2) were from Dr. Dean Sheppard (University of California, San Francisco), and the anti-$\alpha_4\beta_7$ (Act-1) antibody was from Dr. Andrew Lazarovits (University of Western Ontario, Canada).

The migration assays of FIG. 7B were performed using Boyden chambers as previously described in Morla, A., et al., (1994), supra, with slight modifications. In brief, filters were coated with 10 μg/ml of fibronectin, laminin, collagen IV, or vitronectin, overnight at 4° C. Lower chambers were filled with 10% FCS in DMEM. Cells (5×10$^6$) were treated in suspension with media alone (DMEM), fibronectin alone, fibronectin plus III-11-QE-C (SEQ ID NO:15), III$_1$-QE-C (SEQ ID NO:7) alone or sFN (prepared as described above), and then plated (5×10$^4$) onto the filters in the upper chamber and allowed to migrate at 37° C., 5% CO$_2$ for 3 h. The filters were then removed, fixed in 100% methanol and stained with 0.5% Crystal Violet dye in 3.7% paraformaldehyde solution. Cells on the upper surface of the filter were carefully removed with a cotton swab and quantitative analysis of migratory cells was performed by eluting the dye of 3 filters with 100 μl of 0.1 M citrate pH 4.2 in 50% ethanol, and then measuring the optical absorbance at 590 nm.

In conclusion, these data demonstrate that sFN inhibits tumor cell spreading and cell migration. After preincubation with sFN, tumor cells are unable to spread on any of the immobilized human extracellular matrix proteins fibronectin, laminin, collagen IV, and vitronectin (BSA was the negative control). sFN also inhibits the migration of the osteosarcoma and melanoma tumor cells on fibronectin, vitronectin, type IV collagen, and laminin, by about 70%. In these experiments, the difference between sFN and control treatments was clear at all time points assessed and was seen even 24 hours after plating.

EXAMPLE IX sFN is Significantly Superior to Integrin Binding Peptides in the Inhibition of Metastases To demonstrate that tumor cell exposure to sFN is significantly more effective in inhibiting tumor metastases than integrin-binding peptides, the tumor metastasis-inhibitory ability of sFN was compared to the RGD-containing peptides: GRGDSP (SEQ ID NO:16); ACDCRGDCFCG (SEQ ID NO:17) and CRRETAWAC (SEQ ID NO:18). These peptides were synthesized using an Applied Biosystems Model 430A synthesizer (Foster City, Calif.) by standard Merrifield solid phase synthesis and T-butoxycarbonyl chemistry; cyclized after release from the resin by oxidizing with 0.01 M $K_3$ [Fe(CN)$_6$] in 1 mM $NH_4OAc$, pH 8, overnight at 25° C.; lyophilized; and finally purified by reverse-phase high performance liquid chromatography (HPLC). Detailed characterization of and methods of making these peptides are described in: Koivunen, E., et al., *Methods in Enzymology* 245:346–369 (1994); Koivunen, E., et al., *Biotechnology* 13:265–270 (1995); and, Koivunen, E., et al., *J. of Biol. Chem.* 268:20205–20210 (1993), each herein incorporated by reference. The peptides for both sets of experiments were at 1 mg/ml in aqueous buffer.

The GRGDSP (SEQ ID NO:16) peptide blocks the cell attachment activity of several integrins. The CRRETAWAC (SEQ ID NO:18) peptide is an α5β1-directed peptide. The "double cyclic" RGD peptide ACDCRGDCFCG (SEQ ID NO:17) is somewhat selective for $α_v$ integrins, as described in Koivunen, et al., supra, 1995.

Figure 8A:
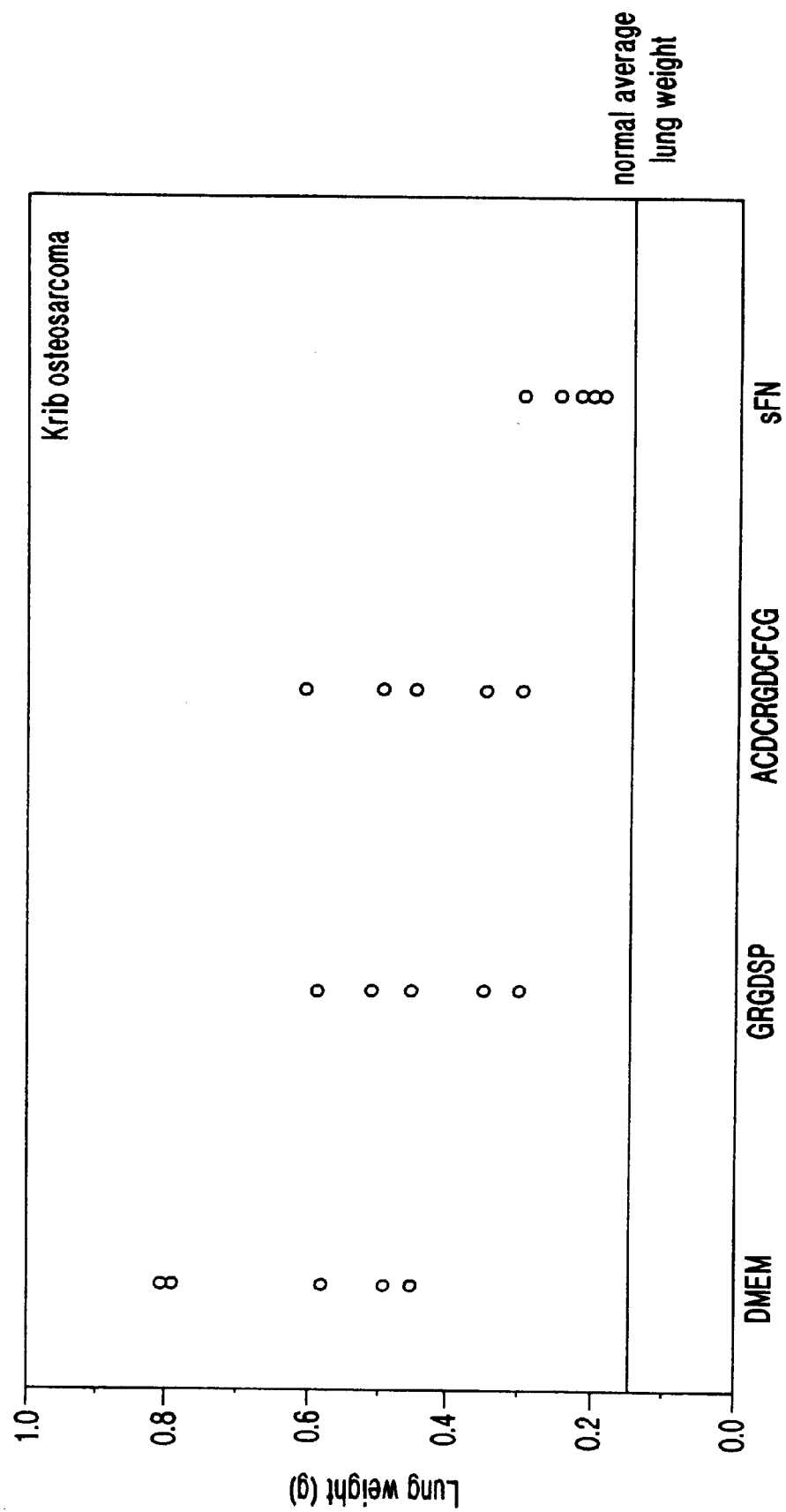
FIGS. 8A and 8B demonstrates that tumor cell exposure to sFN is significantly more efficient in inhibiting tumor metastases than integrin-binding peptides, in particular, the RGD-containing peptides GRGDSP (SEQ ID NO:16), ACDCRGDCFCG (SEQ ID NO:17) and CRRETAWAC (SEQ ID NO:18).
Figure 8B:
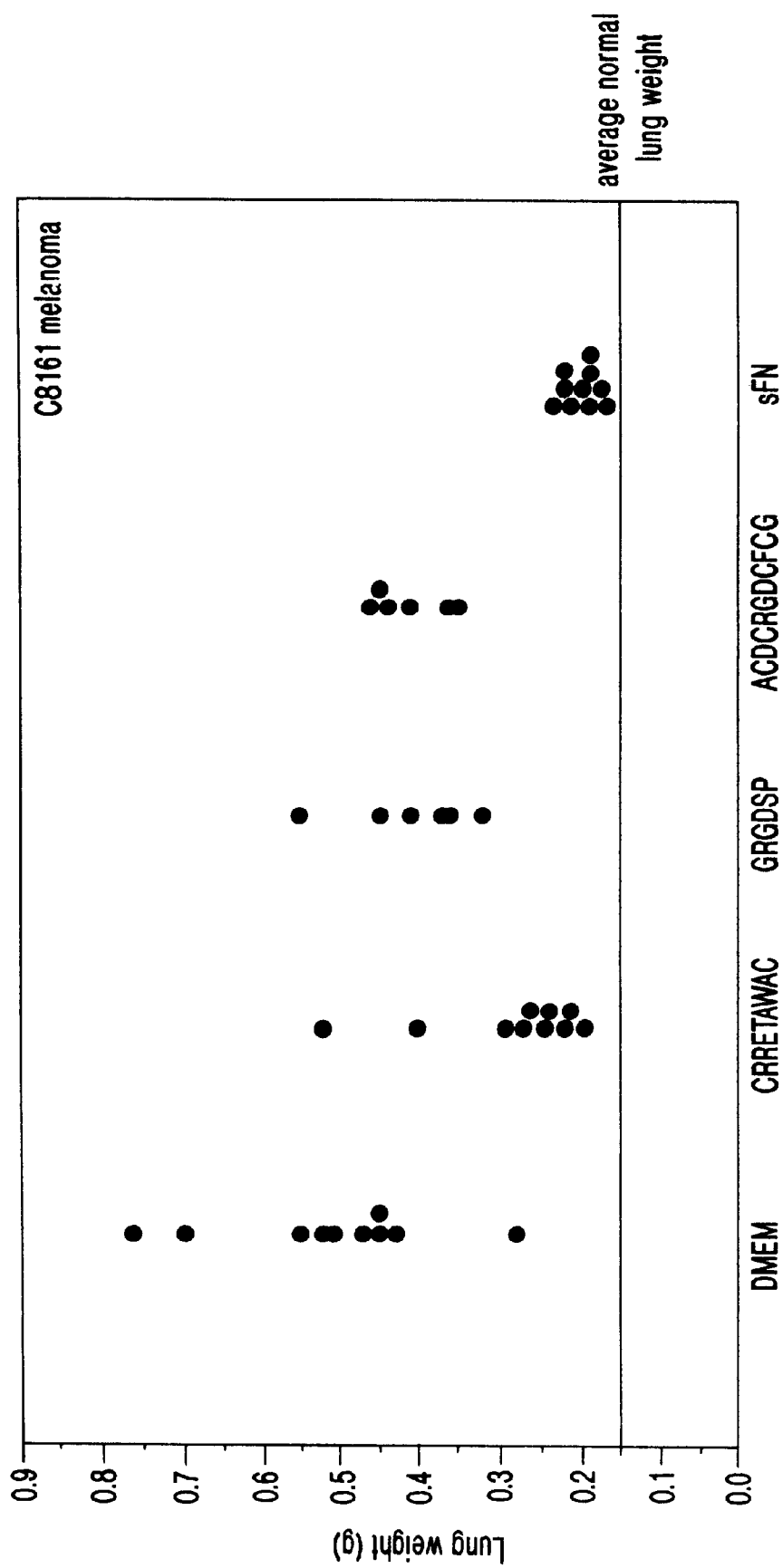

To demonstrate the effect of integrin-directed peptides on Krib osteosarcoma experimental metastasis, in FIG. 8A, Krib tumor cells were pre-incubated with media (DMEM) alone (the vehicle control), peptide GRGDSP (SEQ ID NO:16), peptide ACDCRGDCFCG (SEQ ID NO17), or sFN for 10 minutes before intravenous injection into the tail vein of the mice. In FIG. 8B, C8161 melanoma cells were similarly treated with DMEM alone, the α5β1 integrin-binding peptide CRRETAWAC (SEQ ID NO:18) or sFN. $10^6$ cells per mouse were injected, with 5 mice per experimental group. The peptides for both sets of experiments were used at 1 mg/ml in 200 ul of cell suspension. sFN was made by mixing 100 ug of fibronectin with a 150 molar excess of the III$_1$-QE-C (SEQ ID NO:7) peptide, as described in Example II.

In FIGS. 8A and 8B the average normal lung weight is marked with a line at 0.175 gram. FIG. 8A shows the results of one of 3 experiments in which similar results were obtained. FIG. 8B shows the results of one of 2 experiments in which similar results were obtained. As demonstrated in FIG. 8A, the average lung weight in grams from the Krib cell group pre-treated with DMEM, peptide GRGDSP (SEQ ID NO:16), peptide ACDCRGDCFCG (SEQ ID NO:17), and sFN is 0.622, 0.440, 0.442 and 0.236, respectively. As demonstrated in FIG. 8B the average lung weight in grams from the C8161 melanoma cell group pre-treated with DMEM, CRRETAWAC (SEQ ID NO:18) and sFN is 0.492, 0.288 and 0.198, respectively.

The data presented in FIGS. 8A and 8B clearly demonstrate that sFN is a significantly better inhibitor of metastasis than the tested integrin-binding peptides. Specifically, ex vivo pre-exposure of tumor cells to sFN was a significantly more effective means of inhibiting melanoma and osteosarcoma metastases than the integrin-binding peptides GRGDSP (SEQ ID NO:16) and ACDCRGDCFCG (SEQ ID NO:17) (for osteosarcoma) and CRRETAWAC (SEQ ID NO:18) (for melanoma).

These data also demonstrate that the sFN of the invention as an in vivo anti-metastatic pharmaceutical agent is superior to integrin-binding peptides known to have an anti-metastatic effect.

EXAMPLE X sFN Inhibits Cytokine-Induced Endothelial Cell Growth and Migration sFN can also inhibit endothelial cell growth not associated with tumorigenesis. To demonstrate sFN's inhibitory effect on the cytokine-induced growth of normal endothelial cells, the effect of sFN and the III$_1$-QE-C (SEQ ID NO:7) polypeptide was tested in a chick egg chorio-allantoic membrane (CAM) assay, as described in Brooks, P. C., et al., *Science* 264:569–571 (1994), incorporated herein by reference.

Stimulation of blood vessel growth and the conversion of a tumor to an angiogenic phenotype involves a change in the local balance of blood vessel growth inhibitors and growth stimulators. Of the known angiogenic factors, basic fibroblast growth factor (bFGF) appears to be the most commonly found in tumors. In this assay, bFGF is used as the cytokine to stimulate endothelial cell growth and migration. 11 day chicken embryos and bFGF disks were used as described in Brooks, et al., supra, (1994). Either 500 ng of bFGF alone, this bFGF and 250 uM of III$_1$-QE-C (SEQ ID NO:7), or, bFGF (Collaborative Biomedical Products, Bedford, Mass.) and sFN were added to the disks and placed on top of the exposed CAMs. After 72 hours the number of vessels entering the disk was counted under a dissecting microscope after dissection of the disks, as described in Brooks, et al. (1994). The average number of blood vessels entering the disks treated with: bFGF alone; bFGF and III$_1$-QE-C (SEQ ID NO:7); and, sFN and bFGF, was 9.2, 8.3 and 1.2, respectively. p values are 0.72 and 0.031 for the bFGF/III$_1$-QE-C (SEQ ID NO:7) and sFN/bFGF experiments, respectively, compared to the bFGF alone control experiment. FIG. 9 shows that the sFN/bFGF experiment had fewer endothelial vessels entering the embryonic disk than either the bFGF alone or bFGF and III$_1$-QE-C (SEQ ID NO:7) experiments.

The data in FIG. 9 demonstrates that the invention provides for a general method of inhibiting angiogenesis and cytokine-mediated endothelial cell growth and migration using sFN.

EXAMPLE XII sFN Injected Intraperitoneally Reaches the Circulation

Figure 10A:
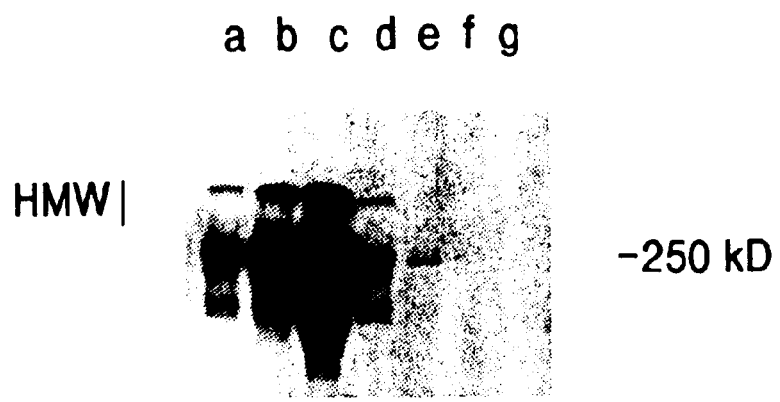
FIGS. 10A and 10B demonstrates that sFN administered intraperitoneally attains sufficient systemic bioavailability to effect the inhibition of metastasis of distally located tumors.

The effectiveness of intraperitoneal sFN in reducing lung colonization and spontaneous metastasis from subcutaneous tumors suggested that sFN may be absorbed systemically from the peritoneal cavity. To determine if sFN was detectable in the plasma, $^{125}$I-sFN was injected intraperitoneally into nude mice and tail vein bleeds were performed at various time intervals.

sFN distribution following intraperitoneal injection was monitored by analyzing blood obtained from tail bleeds. $^{125}$I-fibronectin (100 μg) was incubated with the III$_1$-QE-C (SEQ ID NO:7) polypeptide at a 1:150 molar ratio, for 10 minutes, and injected intraperitoneally into a mouse in 500 μl of DMEM. 20 μl aliquots of blood obtained from the mouse at different time points was analyzed by SDS-PAGE, as shown in FIG. 10A. Lanes a to g of FIG. 10A represent samples obtained at 15 minutes, 30 minutes, 2 hours, 12 hours, 24 hours, 48 hours and 72 hours, respectively. HMW represents high molecular weight material, and the position of a 250 kD MW marker is indicated on the right-hand side of FIG. 10A. This experiment was repeated with similar results, on five different occasions, using a total of 5 mice and different radiolabelled preparations of fibronectin.

Figure 10B:
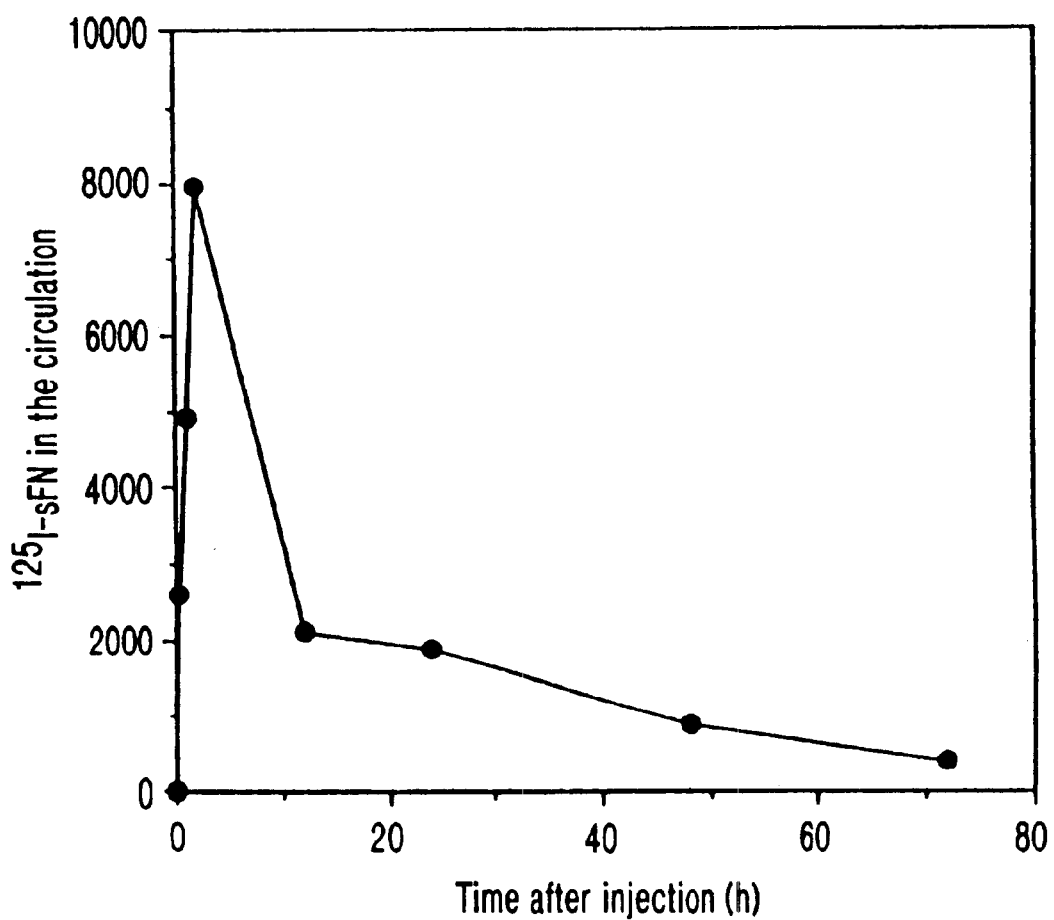

FIG. 10B depicts a graph which demonstrates the amount of radioactivity measured in the high molecular weight material (HMW) of each sample a to g isolated by the SDS-PAGE described above and shown in FIG. 10A.

Specifically, FIG. 10B hows the amount of $^{125}$I-fibronectin radioactivity in counts per minute, cpm, in the HMW material, as indica ted in FIG. 10A, isolated from tail bleed, at the indicated time points. Additionally, FIG. 10B also shows the radioactivity measured in the sample at time zero; this initial time point was not included in the SDS-PAGE analysis depicted in FIG. 10A. Th e experiment shown here is representative of five experiments, all of which produce similar results.

In conclusion, FIG. 10A demonstrates that radioactive material consistent in size with sFN was detected in the blood 15 minutes after the injection and reached peak levels at the 2 hour time point. FIG. 10 also demonstrates that sFN administered intraperitoneally attains sufficient systemic bioavailability to effect the inhibition of metastases of distally located tumors.

EXAMPLE XIII

Administration of sFN and sFN-Generating Compounds to Patients to Inhibit the Formation of Tumor Metastases Administration of sFN or sFN-generating compounds as a pharmaceutical preparation to patients diagnosed with existent primary tumors inhibits the formation of metastases.

sFN can be reconstituted in sterile saline or equivalent intravenous carrier solution. Alternatively, sFN can be generated immediately before administration by mixing sterile fibronectin and a sFN-generating compound in a sterile carrier solution. For example, sFN is mixed with any of the polypeptides: the 14 kDa fibronectin polypeptide fragment (SEQ ID NO:1); the $III_1$ polypeptide (SEQ ID NO:2); the $III_1$-C polypeptide (SEQ ID NO:3); the fibronectin polypeptide fragment SF1 (SEQ ID NO:4); fibronectin polypeptide fragment SF2 (SEQ ID NO:5); the $III_1$-QE-C polypeptide (SEQ ID NO:7); the $III_1$-F polypeptide (SEQ ID NO:6); or, the III-10 polypeptide (SEQ ID NO:8) in a sterile carrier solution.

sFN and sFN-generating compounds can be formulated in a variety of carrier solutions. The sFN or sFN-generating compound is administered IV over a varied dosage range depending on tumor type and location, age, body weight, medical history, and the like. These variation are known or available to one skilled in the art with only routine experimentation. While an effective amount to be administered systemically on a daily basis can be about 0.1 $\mu$g/kg body weight to about 300 mg/kg body weight, the exact dosage amounts and administration schedules will be determined in clinical trials. A formulation for intravenous infusion can be made up to contain 250 ml of sterile Ringer's solution, saline or PBS and up to about 1 gram of sFN. The total effective dose can be administered to the patient as a single dose, either as a bolus or by infusion over a relatively short period of time, or can be administered using a fractionated treatment protocol, in which multiple doses are administered over a more prolonged period of time.

Although the invention has been described with reference to the examples above, it should be understood that various modifications can be made without departing from the spirit of the invention. Accordingly, the invention is limited only by the following claims.

We claim:

1. A method of inhibiting cancer in a subject, comprising administering a superfibronectin-generating compound to the subject, wherein said superfibronectin-generating compound comprises a $III_1$-C or III-1C polypeptide fragment of fibronectin consisting of SEQ ID NO: 3.

2. A method of inhibiting cancer in a subject, comprising administering a superfibronectin-generating compound to the subject, wherein said superfibronectin-generating compound is selected from the group consisting of SEQ ID NOS: 2, 3, and 6.

3. A pharmaceutical composition, comprising a superfibronectin-generating compound and a pharmaceutically acceptable carrier, wherein said superfibronectin-generating compound consists of SEQ ID NO: 2.

4. A pharmaceutical composition comprising a superfibronectin-generating compound and a pharmaceutically acceptable carrier, wherein said superfibronectin-generating compound is selected from the group consisting of SEQ ID NOS: 2, 3, and 6.

5. The method of claim 1, wherein said inhibition comprises inhibiting tumor cell metastasis in said subject.

6. The method of claim 1, wherein said inhibition comprises inhibiting a tumor cell migration in a subject.

7. The method of claim 1, wherein said inhibition comprises inhibiting a tumor cell attachment in a subject.

8. The method of claim 1, wherein said inhibition comprises inhibiting growth of a tumor cell in a subject.

9. The method of claim 1, wherein said cancer is selected from the group consisting of melanoma, osteosarcoma, ovarian, vascular and epithelial cell tumors.

10. The method of claim 9, wherein said epithelial cell tumor is selected from the group consisting of colon carcinoma, breast carcinoma and ovarian carcinoma.

11. The method of claim 9, wherein said vascular cell tumor is selected from the group consisting of hemangioma, Kaposi's sarcoma, lymphangioma, glomangioma, angiosarcoma and hemangioendothelioma.

12. The method of claim 1, wherein said administering is a route of administration selected from the group consisting of an intravenous, an intramuscular, an intradermal, a subcutaneous, an intracranial, an intracerebrospinal, an epidural, a topical and an oral administration.

* * * * *